US007235632B1

(12) United States Patent
Kirszenbaum et al.

(10) Patent No.: US 7,235,632 B1
(45) Date of Patent: Jun. 26, 2007

(54) ISOLATED MAMMALIAN PROTEIN PRESENT AT THE SURFACE OF ALL LYMPHOID PROGENITOR CELLS AND ALL MATURE NK CELLS AND USES THEREOF

(75) Inventors: Marek Kirszenbaum, Paris (FR); Magali Le Discorde, Paris (FR); Stéphane Prost, Pantin (FR)

(73) Assignee: Commissariat a l'Energie Atomique, Paris (FR)

( * ) Notice: Subject to any disclaimer, the term of this patent is extended or adjusted under 35 U.S.C. 154(b) by 401 days.

(21) Appl. No.: 10/129,873

(22) PCT Filed: Nov. 10, 2000

(86) PCT No.: PCT/FR00/03137

§ 371 (c)(1),
(2), (4) Date: Jun. 24, 2002

(87) PCT Pub. No.: WO01/34653

PCT Pub. Date: May 17, 2001

(30) Foreign Application Priority Data

Nov. 12, 1999 (FR) .................................. 99 14241

(51) Int. Cl.
  *C07K 1/00* (2006.01)
  *C07K 14/00* (2006.01)
  *C07K 17/00* (2006.01)
(52) U.S. Cl. .................................... 530/350
(58) Field of Classification Search ................ 530/300, 530/350, 329
  See application file for complete search history.

(56) References Cited

U.S. PATENT DOCUMENTS 6,420,526 B1 * 7/2002 Ruben et al. ................ 530/350

FOREIGN PATENT DOCUMENTS

| WO | WO 9506247 | 3/1995 |
| WO | WO 9520604 | 8/1995 |
| WO | WO 9825959 | 6/1998 |
| WO | WO 9839448 | 9/1998 |
| WO | WO 9931236 | 6/1999 |
| WO | WO 0009552 | 2/2000 |
| WO | WO 01/12660 | * 2/2001 |

OTHER PUBLICATIONS

Attwood Science 2000; 290:471-473.*
Skolnick et al. Trends in Biotech. 2000; 18(1):34-39.*
Whisstock et al ., Quarterly Review of Biophysics, 2003, 36, pp. 307-340.*
Metzler et al. Nature Structural Biol. 1997; 4:527-531.*
Derwent Publ.; Accession No. V59687, Jan. 19, 1999 WO9839448: "Human secreted protein gene 177 clone HE9CM64"; XP002147597 99.2% identity in 1499 bp overlap with SeqldNo. 1 abstract.
Derwent Publ.; Accession No. W74904; Jan. 25, 1999 WO9839448: "Human secreted protein encoded by gene 177 clone HE9CM64"; XP002147598 99.1% identity in 350 aa overlap with SeqIdNo. 2 abstract.
Derwent Publ.; Accession No. V43608; Sep. 24, 1998; J. Escobedo, et al. "Human secreted protein 8 encoding DNA"; XP002147599 99.3% identity in 1149 bp overlap with SeqIdNo. 1 abstract.
Derwent Publ.; Accession No. W63688; Sep. 24, 1998; J. Escobedo, et al. "Human secreted protein 8"; XP002147600 99.6% identity in 254 aa overlap with SeqIdNo. 2 abstract.
Derwent Publ.; Accession No. X97785; Sep. 13. 1999; L. Bougueleret, et al. "Extended human secreted protein coding sequence, SeqIdNo. 350"; XP002147601 98.9% identity in 973 bp overlap with SeqIdNo. 1 abstract.
Derwent Publ.; Accession No. Y36101; Sep. 13, 1999; L. Bougueleret, et al. "Extended human secreted protein sequence, SeqIdNo. 486"; XP002147602 97.1% identity in 209 aa overlap with SeqIdNo. 2 abstract.
Swall Database; EBI, Hinxton, U.K.; Accession No. Q9Y3U9, Nov. 1, 1999; K. Koehrer, et al. "Hypothetical 34.9kDa protein"; XP00214605 cited in the application 99.365% identity in 315 aa overlap with SeqIdNo. 2 abstract.
Ernest Database; EBI, Hinxton, U.K.; Accession No. AW106427, Oct. 21, 1999; M. Marra, et al "Mus musculus cDNA clone IMAGE:2225799 5' similar to WP:Y53C12A.3 CEI4888"; XP002147606 cited in application 97.826% identity in 506 nt overlap with SeqIdNo. 3 abstract.
Derwent Publ.; Accession No. A16633; Jun. 16, 2000; K. Jacobs, et al., "Human secreted protein clone py35_1 nucleotide sequence SeqIdNo. 31"; XP002147603 99.2% identity in 1424 bp overlap with SeqIdNo. 1 abstract.
Derwent Publ.; Accession No. Y94913, Jun. 16, 2000, K. Jacobs et al., "Human secreted protein clone py35_protein sequence SeqIdNo. 32"; XP002147604 identity in 315 aa overlap with SeqIdNo. 2 abstract.

* cited by examiner

*Primary Examiner*—Michail A. Belyavskyi
(74) *Attorney, Agent, or Firm*—Alston & Bird LLP

(57) ABSTRACT

The invention concerns a protein present at the surface of hematopoietic stem cells of the lymphoid cell line and mature NK cells, the corresponding isolated cDNA sequence and their uses as marker of said cells and for preparing antibodies directed against said protein. The invention also concerns the uses of said antibodies for selecting cells expressing at their surface said protein. Said isolated protein has a structure (a) comprising an extracellular domain located between positions 21 and 152, five transmembrane domains located between positions 153 and 295 and a cytoplasmic domain located between positions 296 and 350, with reference to the sequence SEQ ID NO:2; an apparent molecular weight of about 36 to 38 kDa, and its precursor, which comprises in N-terminal of structure (a), a signal sequence of 20 amino acids, is selected in the group consisting of the protein of SEQ ID NO:2, and the proteins having an amino acid sequence having at least 70% identity or at least 85% similarity and preferably at least 95% identity or at least 99% similarity with the sequence SEQ ID NO:2.

3 Claims, 15 Drawing Sheets

```
CGCGGCCGCGTCGACCTCTCCTCGACCCTGGACGTCTACCTTCCGGAGGCCCACATCTTGCCCACTCCGCG        71

M   A   T   T   A   A   P    7
CGCGGGGCTAGCGCGGGTTTCAGCGACGGGAGCCCTCAAGGGAC ATG GCA ACT ACA GCG GCG CCG       136

A   G   G   A   R   N   G   A   G   P   E   W   G   G   F   E   E   N        25
GCG GGC GGC GCC CGA AAT GGA GCT GGC CCG GAA TGG GGA GGG TTC GAA GAA AAC       190

I   Q   G   G   G   S   A   V   I   D   M   E   N   M   D   D   T   S        43
ATC CAG GGC GGA GGC TCA GCT GTG ATT GAC ATG GAG AAC ATG GAT GAT ACC TCA       244

G   S   S   F   E   D   M   G   E   L   H   Q   R   L   R   E   E   E        61
GGC TCT AGC TTC GAG GAT ATG GGT GAG CTG CAT CAG CGC CTG CGC GAG GAA GAA       298

V   D   A   D   A   A   D   A   A   A   E   E   E   D   G   E   F           79
GTA GAC GCT GAT GCA GCT GAT GCA GCT GCT GCT GAA GAG GAG GAT GGA GAG TTC       352

L   G   M   K   G   F   K   G   Q   L   S   R   Q   V   A   D   Q   M        97
CTG GGC ATG AAG GGC TTT AAG GGA CAG CTG AGC CGG CAG GTG GCA GAT CAG ATG       406

W   Q   A   G   K   R   Q   A   S   R   A   F   S   L   Y   A   N   I       115
TGG CAG GCT GGG AAA AGA CAA GCC TCC AGG GCC TTC AGC TTG TAC GCC AAC ATC       460

D   I   L   R   P   Y   F   D   V   E   P   A   Q   V   R   S   R   L       133
GAC ATC CTC AGA CCC TAC TTT GAT GTG GAG CCT GCT CAG GTG CGA AGC AGG CTC       514

L   E   S   M   I   P   I   K   M   V   N   F   P   Q   K   I   A   G       151
CTG GAG TCC ATG ATC CCT ATC AAG ATG GTC AAC TTC CCC CAG AAA ATT GCA GGT       568

E   L   Y   G   P   L   M   L   V   L   T   L   V   A   I   L   L   H       169
GAA CTC TAT GGA CCT CTC ATG CTG GTC CTC ACT CTG GTT GCT ATC CTA CTC CAT       622

G   M   K   T   S   D   T   I   I   R   E   G   T   L   M   G   T   A       187
GGG ATG AAG ACG TCT GAC ACT ATT ATC CGG GAG GGC ACC CTG ATG GGC ACA GCC       676

I   G   T   C   F   G   Y   W   L   G   V   S   S   F   I   Y   F   L       205
ATT GGC ACC TGC TTC GGC TAC TGG CTG GGA GTC TCA TCC TTC ATT TAC TTC CTT       730

A   Y   L   C   N   A   Q   I   T   M   L   Q   M   L   A   L   L   G       223
GCC TAC CTG TGC AAC GCC CAG ATC ACC ATG CTG CAG ATG TTG GCA CTG CTG GGC       784

Y   G   L   F   G   H   C   I   V   L   F   I   T   Y   N   I   H   L       241
TAT GGC CTC TTT GGG CAT TGC ATT GTC CTG TTC ATC ACC TAT AAT ATC CAC CTC       838

H   A   L   F   Y   L   F   W   L   L   V   G   G   L   S   T   L   R       259
CAC GCC CTC TTC TAC CTC TTC TGG CTG TTG GTG GGT GGA CTG TCC ACA CTG CGC       892

M   V   A   V   L   V   S   R   T   V   G   P   T   Q   R   L   L   L       277
ATG GTA GCA GTG TTG GTG TCT CGG ACC GTG GGC CCC ACA CAG CGG CTG CTC CTC       946

C   G   T   L   A   A   L   H   M   L   F   L   L   Y   L   H   F   A       295
TGT GGC ACC CTG GCT GCC CTA CAC ATG CTC TTC CTG CTC TAT CTG CAT TTT GCC      1000

Y   H   K   V   V   E   G   I   L   D   T   L   E   G   P   N   I   P       313
TAC CAC AAA GTG GTA GAG GGG ATC CTG GAC ACA CTG GAG GGC CCC AAC ATC CCG      1054

P   I   Q   R   V   P   R   D   I   P   A   M   L   P   A   A   R   L       331
CCC ATC CAG AGG GTC CCC AGA GAC ATC CCT GCC ATG CTC CCT GCT GCT CGG CTT      1108

P   T   T   V   L   N   A   T   A   K   A   V   A   V   T   L   Q   S       349
CCC ACC ACC GTC CTC AAC GCC ACA GCC AAA GCT GTT GCG GTG ACC CTG CAG TCA      1162

H   *                                                                        350
CAC TGA CCCCACCTGAAATTCTTGGCCAGTCCTCTTTCCCGCAGCTGCAGAGAGGAGGAAGACTATTAA      1231
AGGACAGTCCTGATGACATGTTTCGTAGATGGGGTTTGCAGCTGCCACTGAGCTGTAGCTGCGTAAGTACC      1302
TCCTTGATGCCTGTGGGCACTTCTGAAAGGCACAAGGCCAAGAACTCCTGGCCAGGACTGCAAGGCTCTGC      1373
AGCCAATGCAGAAAATGGGTCAGGTCCTTTGAGAACCCCTCCCCACCTACCCCTTCCTTCCTCTTTATCTC      1444
TCCCACATTGTCTTGGTAAATATAGACTTGGTAATTAAAATGTTGATTGAAGTCTGG                   1501
```

FIGURE 2

ISOLATED MAMMALIAN PROTEIN PRESENT AT THE SURFACE OF ALL LYMPHOID PROGENITOR CELLS AND ALL MATURE NK CELLS AND USES THEREOF

The present invention relates to a protein present at the surface of hematopoietic stem cells of the lymphoid line (pre-T cells, pre-B cells and pre-NK cells) and of mature NK cells, to the corresponding isolated cDNA sequence, and also to uses thereof as a marker for said cells and for preparing antibodies directed against said protein; the present invention also relates to the uses of said antibodies in selecting cells expressing said protein at their surface.

Such antibodies are in particular of use in depleting bone marrow or umbilical cord blood of NK cells, before a bone marrow transplant, for the purpose of reducing rejection of the latter and GVHD.

NK cells represent 10 to 15% of peripheral blood mononuclear cells. It is accepted that they constitute a third lymphocytic line alongside B and T cells; they are defined as large granular lymphocytes (LGLs) which express at their surface neither the CD3 molecular complex nor the α, β, γ chains of the T receptor, bear the CD16 and CD56 markers in humans, NK1.1/NK2.1 in mice, and exert a cytolytic action which does not require the expression of class I or II MHC antigens at the surface of the target cells.

No surface antigen is known which is expressed only by lymphoid line progenitors (pre-T cells, pre-B cells and pre-NK cells) and mature NK cells. Two markers are used to distinguish, in practice, NK cells from the other lymphocyte populations. They are the CD56 antigen and the low-affinity receptor for the immunoglobulin Fc fragment, or CD16.

Although most NK cells may be considered to be CD3−, CD16+, CD56+, a great phenotypical and functional heterogeneity exists in this cell population; most peripheral blood CD56+ lymphocytes also express the CD16 molecule; approximately 10% of peripheral blood NK cells are CD16−, while at the same time expressing CD56 at high density. It has been suggested that CD16−, CD56$^{strong}$ lymphocytes may be the precursors of CD16+, CD56$^{weak}$ NK lymphocytes.

However, since some T cells express both the CD16 molecule and the CD56 molecule, these two molecules are not specific for the peripheral blood NK cell population.

NK cells exhibit a natural cytolytic activity which is exerted directly, without the need for prior immunization, and does not require the presence, on the target cell, of major histocompatibility complex antigens, and antibody-dependent cell-mediated cytotoxicity (ADCC). The ADCC is initiated by the binding of the antibody attached to the target cell with the Fc receptor (CD16) of the effector cell. NK cells therefore play an important role in the host's defence against viral infections and in immune surveillance with respect to tumor cells.

NK cells may induce a primitive form of allorecognition which contributes to rejection of the graft in an allogenic transplant and also to graft versus host disease (GVHD). For these reasons, reliable identification of NK cells in the mononuclear cell population, as well as of all of the lymphoid line precursor cells, is important.

A certain number of documents propose methods for depleting bone marrow of NK cells; in these various methods, NK cells are selected using markers such as CD56, CD16, PEN5 or NKB1:

* PCT International Application WO 95/20604 describes an antigen present on NK cells and T cells. This antigen was named NKB1. A monoclonal antibody directed against this antigen is also described (DX9 antibody). This NKB1 marker has the following properties:
  it binds specifically to the DX9 antibody,
  it has a molecular weight of about 50 kDa,
  it is a glycosylated protein; the molecular weight of the glycosylated protein is approximately 70 kDa,
  the natural form of the protein contains sialic acid residues and is in particular phosphorylated,
  the NKB1 markers are expressed by a subset of NK cells and by a subset of T cells.

PCT International Application WO 95/06247 describes an NK cell-specific antigen in the form of a pair of glycoproteins, designated PEN5α and PEN5β having an apparent molecular weight of 120-150 and 210-245 kDa, respectively.

The unique epitopes of the PEN5α/PEN5β pair of glycoproteins are preferably expressed by a subpopulation of peripheral blood NK cells of phenotype CD16+, CD56$^{dim}$; they are not present on CD3+ T lymphocytes or CD20+ B lymphocytes.

These methods result in the depletion of CD56+, CD16+ mature NK cells or PEN5, NKB1 premature NK cells, but do not deplete the progenitors which, after transplant, may differentiate into mature cells which will cause graft rejection.

Other documents confirm this lack of specific markers; for example, in the article by E. Dominguez et al. (Immunol., 1998, 94, 109-114), it is specified that no unique marker for NK cells has yet been identified, and that they are distinguished, conventionally, by the fact that they express CD56.

It emerges from this set of documents that no markers exist which are specific, firstly, for NK cells or, secondly, for all lymphoid line progenitors.

The Applicant has therefore given itself the aim of providing a marker specific for mature NK cells and also for all undifferentiated cells of the lymphoid line, in order to make it possible in particular to deplete the bone marrow of lymphoid line precursor cells (pre-NK, pre-T and pre-B cells) and of mature NK cells, in particular before a bone marrow transplant, for the purpose of reducing rejection of the latter and GVHD.

In fact, surprisingly, the Inventors have now found that a marker exists which is specific both for all lymphoid progenitor lines (pre-T, pre-B and pre-NK lines) and for mature NK cells.

A subject of the present invention is an isolated protein, characterized:
  in that it is present at the surface of all lymphoid progenitor cells and all mature NK cells,
  in that it has a structure (a) comprising an extracellular domain located between positions 21 and 152, five transmembrane domains located between positions 153 and 295 and a cytoplasmic domain located between positions 296 and 350, with reference to the sequence SEQ ID NO:2,
  in that it has an apparent molecular weight of approximately 36-38 kDa, and
  in that its precursor, which comprises, at the N-terminal of the structure (a), a 20 amino acid signal sequence, is selected from the group consisting of the protein of SEQ ID NO:2, and the proteins which have an amino acid sequence having at least 70% identity or at least 85% similarity, and preferably at least 95% identity or at least 99% similarity, with the sequence SEQ ID NO:2.

The term "precursor" is intended to mean the protein including the signal sequence.

"The identity" of a sequence relative to a reference sequence is assessed as a function of the percentage of amino acid residues which are identical, when the two sequences are aligned so that they correspond to one another to a maximum.

A protein which has an amino acid sequence having at least X % identity with a reference sequence is defined, in the present invention, as a protein the sequence of which may include up to 100-X modifications per 100 amino acids of the reference sequence. For the purpose of the present invention, the term "modifications" includes consecutive or dispersed deletions, substitutions or insertions of amino acids in the reference sequence.

"The similarity" of a sequence relative to a reference sequence is assessed as a function of the percentage of amino acid residues which are identical or which differ by conservative substitutions, when the two sequences are aligned so as to correspond to one another to a maximum. For the purpose of the present invention, the term "conservative substitution" is intended to mean the substitution of one amino acid with another which has similar chemical properties (size, charge or polarity), which does not generally modify the functional properties of the protein.

A protein which has an amino acid sequence having at least X % similarity with a reference sequence is defined, in the present invention, as a protein the sequence of which may include up to 100-X nonconservative modifications per 100 amino acids of the reference sequence. For the purpose of the present invention, the term "nonconservative modifications" includes consecutive or dispersed deletions, nonconservative substitutions or insertions of amino acids in the reference sequence.

A certain number of documents describe proteins having a certain homology with the proteins according to the invention:

PCT Application WO 98/39448 (Human Genome Sciences Inc) describes gene 177, clone HE9CM64 which potentially encodes a secreted protein (nucleic acid sequence: SEQ ID NO:187, peptide sequence: SEQ ID NO:489); however, only the mRNA has been detected in the brain and, to a lesser degree, in the kidney, the placenta, the smooth muscle, the heart and the lung. The protein potentially encoded by said mRNA has never been isolated and no real function is associated with this protein, which is not clearly defined at its N- and C-terminal ends, which may vary.

PCT International Applications WO 98/25959 (Chiron Corp.) and WO 99/31236 (Genset), and also the information relating to the sequences accessible in the SWALL DATABASE under the No. Q9Y3U9, or the information relating to the sequences accessible in the EMEST DATABASE, under the No. AW106427, describe sequence fragments having homology with a fragment of the sequence SEQ ID NO:2; however, in the application pending, the homology is clearly defined relative to the complete sequence SEQ ID NO:2; in addition, none of those documents discloses proteins which are surface markers for early lymphoid line progenitors and for mature NK cells.

Specifically, the protein according to the invention has the following properties:

it is present at the surface of the cells of the NK cell differentiation line, from the very early progenitors to the mature cytotoxic cells, and of the other early progenitors of the lymphoid line (pre-B and pre-T), it has an apparent molecular weight of approximately 36-38 kDa, measured by SDS-PAGE electro-phoresis on a 12% gel under reducing conditions, it comprises an extracellular domain which has at least the sequence SEQ ID NO:6, 7 or 24, and it has a structure comprising an extra-cellular domain, five transmembrane domains and a cytoplasmic domain; it is preferably selected from the group consisting of the protein having the formula SEQ ID NO:25 (human protein which comprises 330 amino acids) and the proteins of other mammals, the extra-cellular domain of which consists of the fragments of sequence SEQ ID NO:6, 7 or 24.

Said surface molecule or protein, named KLIP-1 antigen, is therefore specifically present on the NK cell differentiation line, from the very early progenitors to the cytotoxic mature cells, and also on the other early progenitors of the lymphoid line (pre-B and pre-T).

With reference to human SEQ ID NO:2, amino acids 1-20 correspond to the signal sequence; amino acids 21-152 (human SEQ ID NO:7; murine SEQ ID NO:24; porcine SEQ ID NO:6) correspond to the extracellular domain; amino acids 153-295 (SEQ ID NO:8) correspond to the five transmembrane domains (143 amino acids) and amino acids 296-350 (SEQ ID NO:9) correspond to the cytoplasmic domain (54 amino acids).

The following cells are KLIP-1+:

.CD34+,CD38− early hematopoietic progenitors of the bone marrow, of umbilical cord and of fetal liver .CD34+,CD38+ differentiated progenitors .CD4+,CD8+ pre-T progenitors (neonatal thymus)

.CD19+, CD10−, CD20− pre-B progenitors

.CD56+, CD16+, CD19−, CD3−, CD33− mature NK cells.

The fact that this KLIP-1 antigen is present both on the earliest progenitors and on the differentiated progenitors and mature NK cells makes it possible to obtain an NK cell-depletion of the bone marrow in the presence of anti-KLIP-1 antibodies, which constitutes a better prevention of graft rejection and a potential treatment for autoimmune diseases.

The KLIP-1 antigen as described above may be considered to be a marker specific for NK cells (early and mature) and, in particular, a marker for mature cells since, in peripheral blood, no other cell of the lymphoid line (mature B cells and T cells) exhibits such an antigen.

A subject of the present invention is also fragments of said protein, characterized in that they are selected from the group consisting of fragments comprising between 7 consecutive amino acids and 132 consecutive amino acids of the extracellular domain of said protein, fragments comprising between 7 consecutive amino acids and 143 consecutive amino acids included within the transmembrane domains of said protein and fragments comprising between 7 consecutive amino acids and 54 consecutive amino acids included within the cytoplasmic domain of said protein and the fragment of sequence SEQ ID NO:4; among said fragments, mention may be made of the sequences SEQ ID NO:6, 7, 8, 9 and 24.

A subject of the present invention is also the isolated nucleic acid sequences (in particular cDNA sequences) encoding said protein or fragments thereof, as defined above, of human or animal origin, and also the complementary nucleic acid sequences.

Among these sequences, mention may be made of:

the cDNA encoding the human KLIP-1 antigen, which has the sequence SEQ ID NO:1 and comprises 1501 bp;

it is obtained from the klip-1 gene located on chromosome 6, in the region 6p21.2-6p21.1;

the sequence encoding the human KLIP-1 protein, which is between base 116 and base 1165 of the sequence SEQ ID NO:1 (SEQ ID NO:10);

the sequence encoding the extracellular domain of the human (SEQ ID NO:11), murine (SEQ ID NO:3 and SEQ ID NO:23) or porcine (SEQ ID NO:5) KLIP-1 protein;

the sequence encoding the transmembrane domains of the human KLIP-1 protein (SEQ ID NO:12); the positions of the 5 transmembrane helices are as follows: 153-169, 181-209; 218-237, 243-261 and 275-295; and the sequence encoding the cytoplasmic domain of the human KLIP-1 protein (SEQ ID NO:13).

A subject of the present invention is also nucleic acid fragments, characterized in that they comprise at least 8 bp of the various cDNA sequences as defined above. Such fragments may in particular be used as probes or as primers for amplification or for reverse transcription, for example the sequences SEQ ID NO:16-20.

A subject of the present invention is also antibodies, characterized in that they specifically recognize the KLIP-1 surface antigen according to the invention, which is specific for the NK cell differentiation line, from the very early progenitors to the cytotoxic mature cells, and for the other early progenitors of the lymphoid line (pre-B and pre-T), or a fragment of this antigen.

According to an advantageous embodiment of said antibodies, they are directed against one of the abovementioned regions of the KLIP-1 antigen, preferably against the extracellular domain of the KLIP-1 protein.

In accordance with the invention, said antibodies are either polyclonal antibodies or monoclonal antibodies.

In addition, the anti-KLIP-1 antibodies also make it possible to obtain depletion of lymphoid progenitor cells (pre-B and pre-T).

In bone marrow transplantation, the antibodies, fragments and derivatives according to the invention may be used to deplete the bone marrow of KLIP-1+ cells ex vivo, before transplanting the donor's marrow into the recipient's marrow.

At the current time, no marker exists for early NK cells: KLIP-1 thus constitutes the first marker present both on the entire NK cell differentiation line and on the other early lymphoid lines.

A subject of the present invention is also a method for selectively removing the KLIP-1+ cells from a biological sample comprising a heterogeneous population of cells, which method comprises:

bringing said biological sample into contact with an antibody directed against a surface molecule according to the invention, which is specific for the NK cell differentiation line, from the very early progenitors to the cytotoxic mature cells, and for the other early progenitors of the lymphoid line (pre-B and pre-T), or a fragment of this molecule, and removing the cells which bind to said antibody.

According to an advantageous embodiment of said method, said antibody is attached to a solid support, such as magnetic beads or other immunoadsorbent supports (CNBr Sepharose, for example).

In accordance with said embodiment, in order to deplete the biological sample, and in particular the bone marrow, umbilical cord blood or fetal liver, of cells comprising the KLIP-1 antigen at their surface, these cells are attached to immunomagnetic beads covered with anti-KLIP-1 antibodies, preferably antibodies directed against the extracellular domain of the KLIP-1 protein.

Advantageously, said method may be carried out in order to enrich a biological sample in human mature or progenitor NK cells using mixtures of human cells originating from fetal liver, from umbilical cord blood, from fetal, neonatal or adult bone marrow or from peripheral blood.

A subject of the present invention is also the use of the cells of the bone marrow, of umbilical cord blood, of fetal liver or of any other fetal or adult hematopoietic tissue, depleted of NK cells and/or of lymphoid progenitors, obtained using the method as defined above, for preparing a product which can be transplanted.

A subject of the present invention is also a method for detecting and/or quantifying and/or isolating the NK cells and/or the lymphoid cell progenitors (pre-B, pre-T and pre-NK) in a hetero-geneous population of cells, which method is characterized in that it comprises:

bringing a biological sample comprising a heterogeneous population of cells into contact with an antibody directed against the KLIP-1 protein or a fragment of this protein, according to the invention, and detecting the formation of the cell-antibody complex, in particular using a standard immunological method.

According to an advantageous embodiment of said method, when said sample consists of bone marrow, of umbilical cord blood, of fetal liver or of any other hematopoietic tissue (fetal or adult), it may also comprise bringing the cells which have formed a complex with said antibody into contact with an antibody specific for pre-B cells (anti-CD19 antibody or anti-CD10 antibody) and/or for pre-T cells (anti-CD3 antibody, anti-CD4 antibody or anti-CD8 antibody).

A subject of the present invention is also the use of the antibodies as defined above, in the treatment of autoimmune diseases.

A subject of the present invention is also a method for diagnosing malignant and benign hemopathies, characterized in that it comprises detecting a nucleic acid sequence as defined above, in a biological sample.

Specifically, determination of the modulation of the expression of the KLIP-1 gene and/or of the mutations of the sequence of said gene make it possible to diagnose a hemopathy.

A subject of the present invention is also a kit for detecting and/or quantifying and/or isolating the NK cells and/or the lymphoid cell progenitors (pre-B, pre-T and pre-NK), characterized in that it comprises, besides useful amounts of buffers suitable for carrying out said detection, suitable doses of an antibody directed against the KLIP-1 antigen or a fragment of this antigen according to the invention, optionally conjugated to an immunoadsorbent solid support, and suitable doses of a reagent for revealing the cell-antibody complex possibly formed.

A subject of the present invention is also the use of the protein fragments according to the invention comprising at least 7 consecutive amino acids of the extracellular domain as defined above, as a reagent for detecting NK cells.

Besides the arrangements above, the invention also comprises other arrangements, which will emerge from the following description, which refers to examples of implementation of the method which is the subject of the present invention and also to the attached drawings in which:

FIG. 1 represents an RNA differential display (RDD); in this figure, the lanes 1 correspond to the yolk sac, the lanes 2-5 correspond to fetal liver and lane 6 corresponds to a control;

FIG. 2' represents a model for the transmembrane portion;

It should be clearly understood, however, that these examples are given purely by way of illustration of the subject of the invention, of which they in no way constitute a limitation.

EXAMPLE

Cell and Tissue Methods

Human embryonic tissues were obtained from voluntary terminations of pregnancy, in accordance with French legislation. The project was approved by the local committee for ethics, and prior informed consent was obtained from all the mothers. The stage of development (of gestation) of each embryo was determined by anatomical criteria. The yolk sac, the dorsal aorta with the splanchnopleure (AGM region) and the liver were dissected under a binocular lens and were immediately prepared for extraction of the RNA or were frozen in liquid nitrogen and stored at −80° C. Because of the various developmental stages of the embryos, the dissected tissues were treated separately and not mixed.

Umbilical cord blood was collected from full-term newborn babies in good health (healthy), immediately after birth, with the agreement of the mother.

Bone marrow and peripheral blood were collected from normal adult donors, in accordance with the institutional guidelines. Mononuclear cells were obtained by centrifugation in a Ficoll-Hypaque gradient under standard conditions. The normal postnatal thymocytes were isolated by elution from pieces of thymus taken during heart-correcting operations. For the cytofluorometric analysis, the mononuclear cells were used fresh or frozen.

RNA Differential Display (RDD), Cloning and Sequencing

Figure 1:
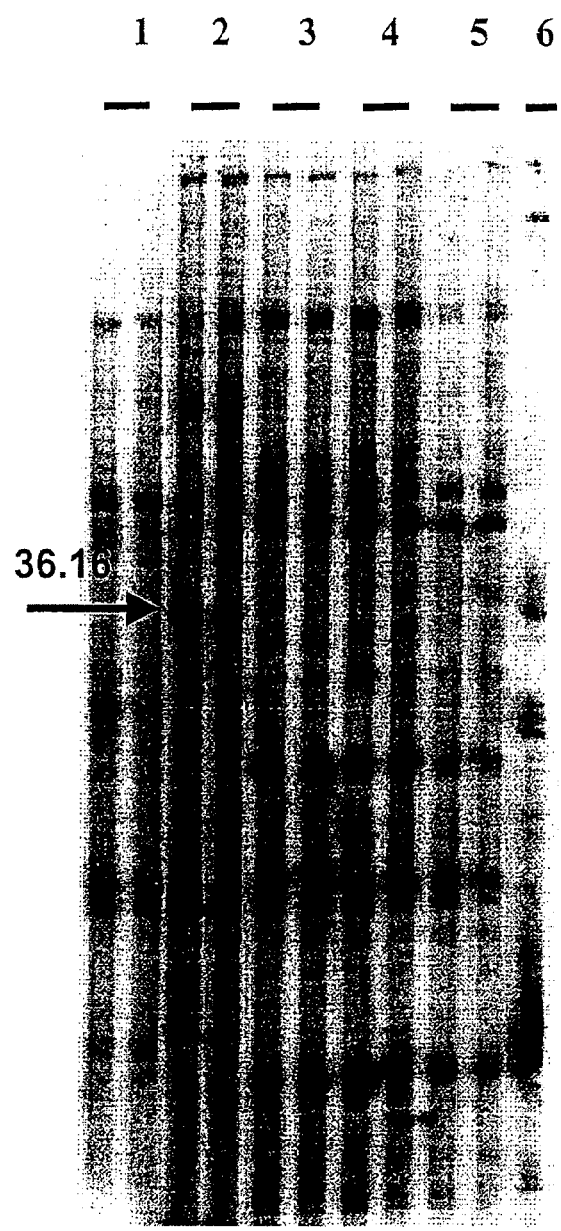

The total mRNA was extracted from the tissues examined (fresh or frozen) using the RNA NOW reagent (Ozyme, France), in accordance with the manufacturer's recommendations, and treated with RNAse-free DNAseI (Boehringer Mannheim, Meylan, France) for 1 hour at 37° C., and then precipitated with ethanol. The quality of the RNA was verified by electrophoresis on a 1.5% agarose denaturing gel. The cDNAs were prepared from 5 µg of total RNA, in the presence of 5'T$_{11}$XY (X=A, G or C; Y=A, T, G or C) (SEQ ID NO:14) as the 3' anchoring primer and of M-MLV reverse transcriptase (GIBCO-BRL, Life Technologies, Cergy, France), at 42° C. for 1 hour. The amplifications by reverse PCR were performed with the same 3' anchoring primer (antisense primer) and 10 arbitrary nucleotides in 5' (sense primer), in the presence of 5 µCi of [α$^{32}$P]-dCTP (Amersham France, Les Ulis, France). The results illustrated in FIG. 1 were obtained with the following primers: 5'-T$_{11}$GG (SEQ ID NO:14) and 5'-GTTGCGATCC (SEQ ID NO:15). The PCR products were heat-denatured for 3 minutes at 80° C. in a sequencing stop buffer and separated by electrophoresis on a 6% polyacrylamide denaturing gel. The gels were dried, without fixing, on 3MM Whatman filter paper and exposed for 16 hours on Kodak Biomax films (Amersham France, Les Ulis, France).

The bands which regularly appeared as being differential in two independent amplifications were excised, eluted from the gel, reamplified under the same reaction conditions (35 cycles), analyzed on 2% agarose gel and cloned into a vector pCRII (TA Cloning Kit, Invitrogen, Leek, The Netherlands). A minimum of 40 individual recombinant (white) colonies were recovered and the presence of the inserts was tested by PCR with flanking primers from the vector. Several recombinant plasmids were amplified by miniprep, purified using the Qiagen kit (Qiagen, Courtaboeuf, France) and then radiolabeled with [α$^{32}$P]-dCTP. These plasmids were used as probes to eliminate the similar clones. The nonredundant clones were sequenced manually using the enzymatic method with dideoxynucleotides (Sanger method) in the presence of Sequanase® 2.0 and flanking primers from the vector, according to the manufacturer's protocols (US Biochemicals, Cleveland, Ohio). Sequence homology searches were performed, via INFOBIOGEN/BLAST (http://www.infobiogen.fr), on GenBank and on the EMBL databases.

Isolation of the KLIP-1 cDNA (Clone No. 36-16) from Embryonic Hematopoietic Tissues by PCR-RDD The profile expression of the gene during human embryogenesis was studied. The transcripts expressed differentially at day 32 YS (yolk sac) and from day 27 to day 49 FL (fetal liver) were examined using the PCR-RDD technique. Clone 36-16 was isolated from the RDD gel and its differential expression was confirmed by the strong expression at day 25 (yolk sac), weak expression at day 32 (yolk sac) and strong expression at day 28 [AGM (aorta-gonad-mesonephros region)], as at day 28 (fetal liver), followed by the decrease in expression at the late stages (fetal liver).

Cloning of the Complete cDNA and Analysis of the Deduced Protein

A human lung cDNA library (Plasmid MATCHMAKER Library, Clontech, Paris, France) in the vector pACT2 was used. The 36-16 cDNA clones were obtained by screening 1×10$^6$ colonies of the cDNA library, using a $^{32}$P-labeled 255 bp 36-16 insert as a probe for the hybridization on Hybond N+Nylon membranes. The positive clones were tested by PCR with the flanking primers from the vector and were confirmed by hybridization with the radiolabeled 36-16 insert. Two clones exhibited a positive hybridization signal and an appropriate size of approximately 1600 pb, in agreement with the Northern blotting results. One of them was sequenced by the Sanger method, using fluorescent terminators and an Applied Biosystems ABI sequencer (Pharmacia, Orsay, France).

Characterization of the Complete KLIP-1 cDNA (36-16) and Deduced Protein

Figure 2:
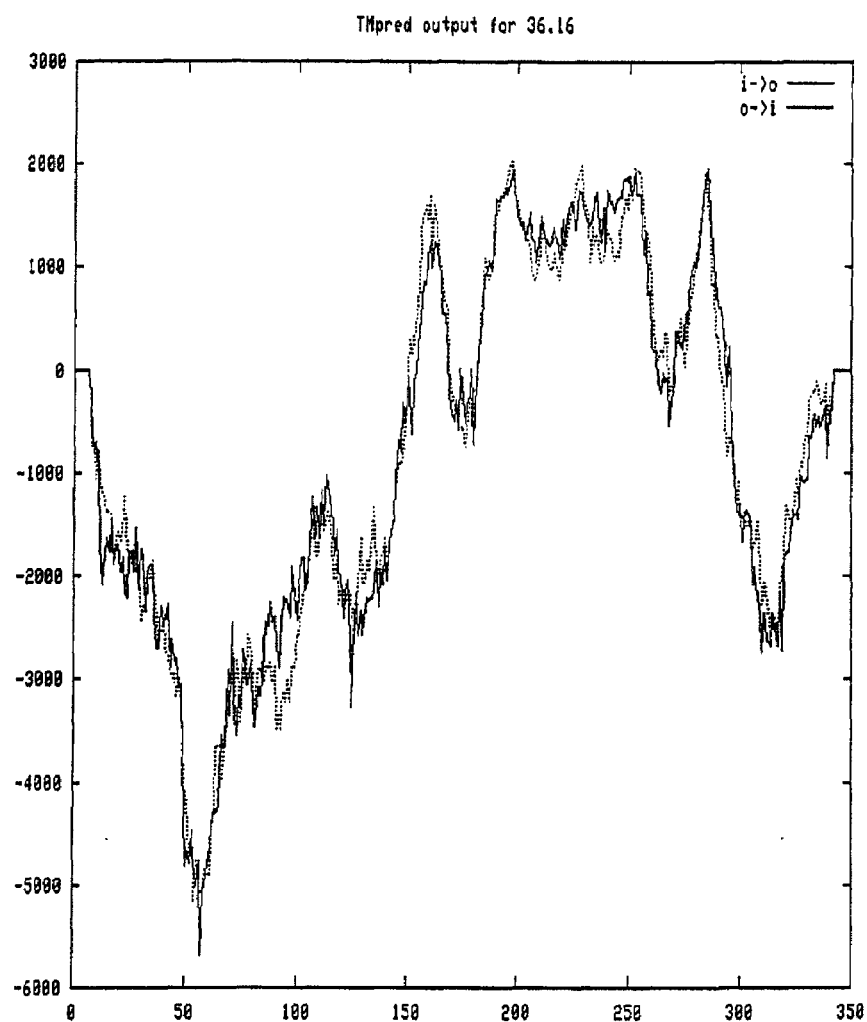
FIG. 2 represents the human KLIP-1 nucleotide and protein sequences.

The complete cDNA comprises 1501 bp and has a single open reading frame of 1050 bp with a 5' UTR of 115 bp and a 3' UTR of 333 bp, which predicts a 350 amino acid protein, named KLIP-1, with a molecular weight of 38.2 kDa (FIG. 2). Analysis of the hydrophobicity of the KLIP-1 sequence suggests 5 strong TM helices (FIG. 2'). The KLIP-1 protein thus has a signal peptide from amino acid (aa) 1 to 20, an extracellular domain of 132 aa (aa 21 to 152), 5 TM domains of 143 aa (aa 153-295) and a C-terminal cytoplasmic tail of 54 aa (aa 296 to 350).

RH (Radiation Hybrid) Chromosomal Mapping

The cDNA clones were screened by PCR, against the GeneBridge4 whole genome radiation hybrid (PH) panel (Research Genetics, Huntsville, Ala.), which contains 93 clones from hamster-human chimeras. Each clone was tested individually in two independent PCR amplifications with two primers specific for the 3'UTR: 1265F (5'-ACCCCACCTGAAATTGG) (SEQ ID NO: 16) and 1522R (5'-GAGATAAAGAGGAAGGAAGGAAGG) (SEQ ID NO: 17) under the following conditions: 94° C., 45 sec; 61° C., 1 min; 72° C., 45 sec, for 10 cycles, and then 94° C., 45 sec; 58° C., 1 min; 72° C., 45 sec, for 30 cycles, terminated by a 10-min incubation at 72° C. The Southern blots containing the PCR products and the human (positive) or hamster (negative) control DNAs were hybridized with a $^{32}$P-labeled specific internal probe and washed under stringent conditions, 0.2×SSC+0.2% SDS at 60° C., and were then exposed for 16 hours to Kodak Biomas films. A single specific human band was observed at the expected size of 257 bp. The hybridization data derived from the screening profile were submitted to the Whitehead Institute (MIT Center for Genome Research RH Mapper Server and the KLIP-1 gene was linked to physical markers. The GeneMap'98 physical map was used to produce therefrom the cytogenetic location of the band corresponding to the RH mapping results. In order to confirm the location of the KLIP-1 gene, PCR amplifications with the primers 1265F (SEQ ID NO:16) and 1522R (SEQ ID NO:17), specific for the 3' UTR of KLIP-1, hybridized with the $^{32}$P-labeled internal probe 5'-CTGTGGGCACTTCTGAAAGG (SEQ ID NO:18), were carried out on YAC clones 907_H_2 and 939_E_12 (Centre d'Etudes du Polymorphisme Humain [Center for Studies on Human Polymorphism], Paris, France) containing, respectively, the markers D6S271 and D6S459. These markers surround the region of KLIP-1 on chromosome 6 and the marker AFM136YD12. The genomic DNA and the YAC clone 979_B_3, located on chromosome 1 (D1S444), were used as a positive and negative control, respectively.

Chromosomal Location of the KLIP-1 Gene (36-16) by Typing of the RH Chimera Panel The mapping analysis positions the KLIP-1 sequence between the structural markers D6S271 and AFM165YD12 of GeneBridge4, respectively 5.66 cR from D6S271 and 2.84 cR from AFM65YD12 at LOD 1.08.

Figure 3:
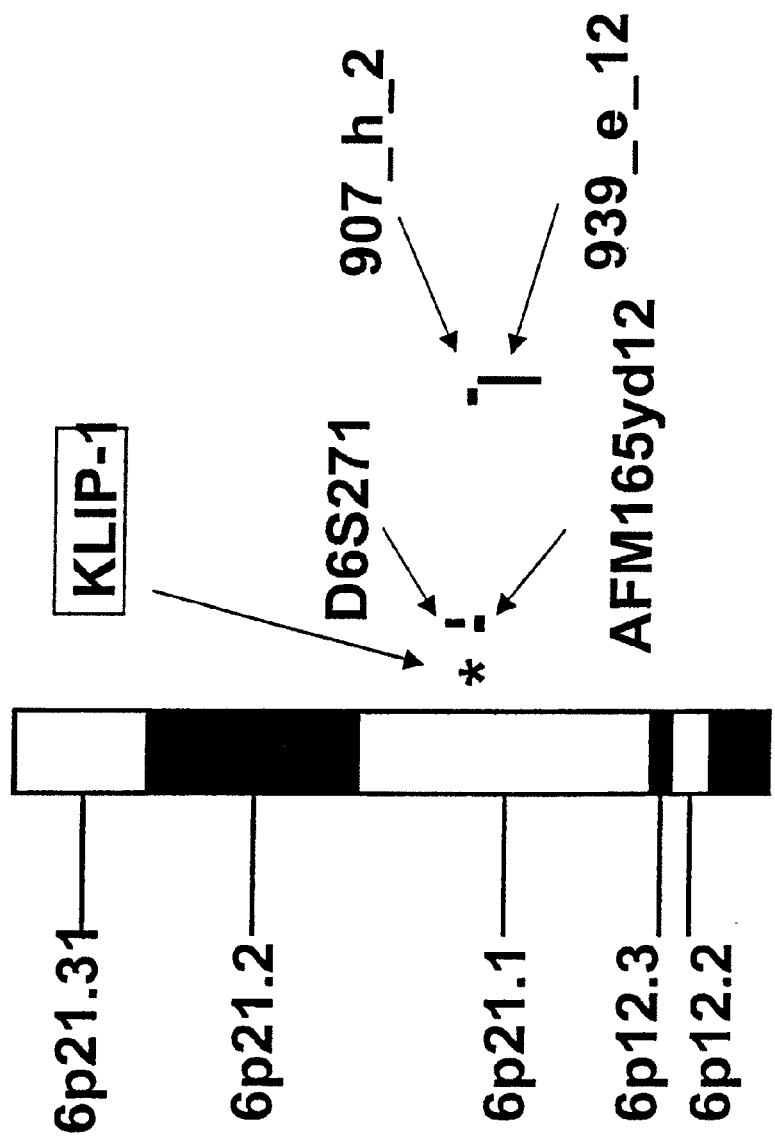
FIG. 3 represents the chromosomal location of the KLIP-1 gene.

The GeneMap'98 physical map, linked to the cytogenic band location, located the KLIP-1 gene at 6p21.1-6p21.2 of chromosome 6. PCR amplification, with the primers used for the RH chimeras, of CEPH YAC clones No. 907_h_2 and No. 939_e_12, containing the markers D6S271 and AFM165YD12, respectively, confirms this location (FIG. 3).

Generation of the Recombinant KLIP-1 Protein

Figure 4A:
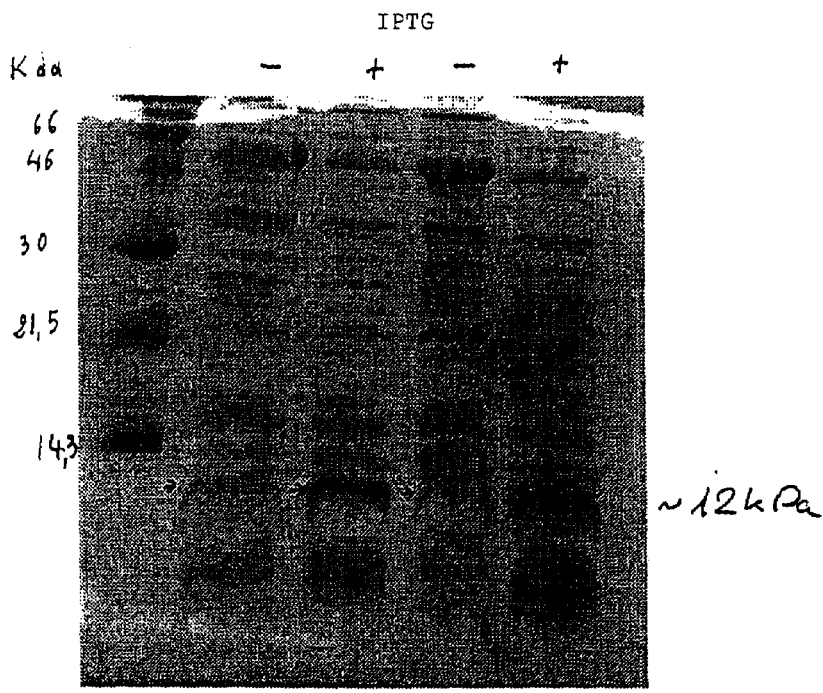
FIG. 4 illustrates the induction of expression of a fusion protein comprising the extra-cellular domain of the human KLIP-1 protein (12 kDa)
Figure 4B:
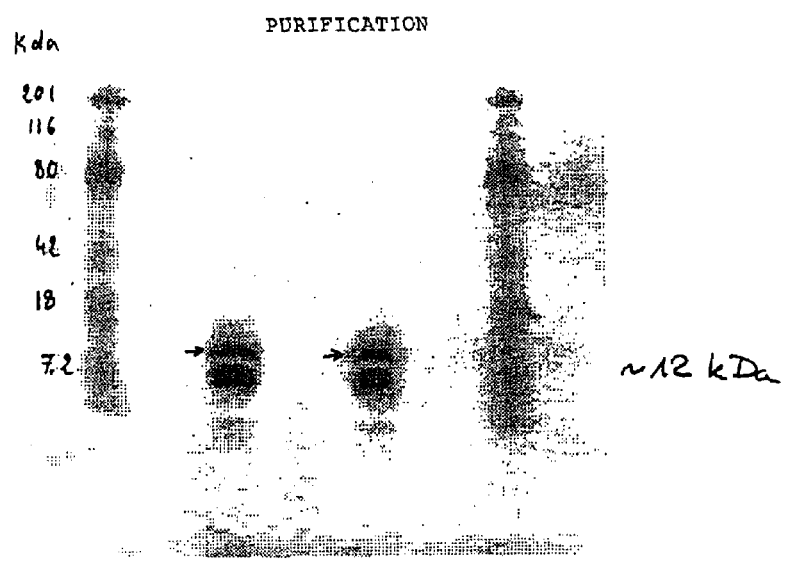

The cDNA, obtained after PCR amplification with the primers 180F: 5'-TCGAAGAAAACATCCAGGGC (SEQ ID NO:19) and 556R: 5'-AGAGGTCCATAGAGTTC-CACC (SEQ ID NO:20), encodes an extracellular protein of 134 aa from positions 22 to 156. The PCR product was ligated to the His6x-tagged pQE-31 expression vector (QIAexpress System, Qiagen, Courtaboeuf, France), and was then transformed into the M15 strain carrying the repressor plasmid pREP4. The construct and the positive transformant were screened, by direct sequencing, for correct insertion and in-frame conservation. The 12 kDa His6X-tagged protein, induced with IPTG (FIG. 4A) was purified on Ni-NTA agarose under denaturing conditions and was visualized by Coomassie blue staining on an SDS/PAGE gel at 12% (FIG. 4B).

Generation and Purification of the KLIP-1 Polyclonal Antibody

Antibodies (Ab) were generated by immunizing White New Zealand rabbits, on a monthly basis, with 100 µl of purified 12 kDa recombinant extracellular protein in an incomplete Freund's adjuvant. After 3 injections, the serum was collected and then all the IgGs were purified using Hitrap protein G affinity columns (Pharmacia Biotech, Orsay, France) and the nonspecific anti-*E. coli* rabbit antibodies were removed using an immobilized *E. coli* lysate (Pierce, Rockford, Ill.).

Revelation by Western Blotting

Figure 5:
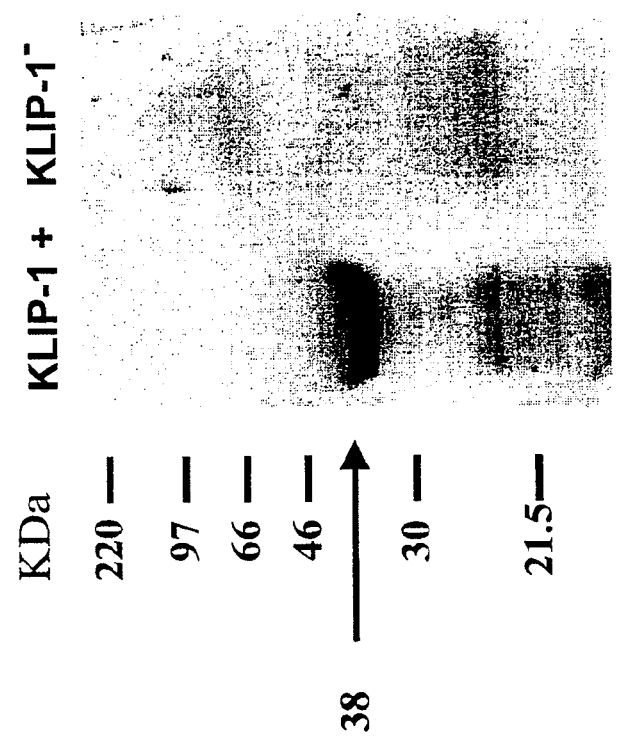
FIG. 5 illustrates a Western blot on the KLIP-1+ and KLIP-1− populations.

Total bone marrow or bone marrow enriched in KLIP-1+ cells, and cord blood mononuclear cells, were lyzed for 10 minutes at 100° C. in buffer containing 50 mM Tris (pH 6.8), 10% glycerol, 2% SDS, 5% 2-mercaptoethanol and 0.02% bromophenol blue. The proteins (equivalent of $3 \times 10^5$ cells) were separated by SDS-PAGE on a 12% gel and electrotransferred onto Hybond C-Extra nitrocellulose membranes (Amersham, Les Ulis, France). The membranes were blocked with low-fat powdered milk in 1×PBS, 0.2% Tween 20, for 1 hour at room temperature, and were incubated with the anti-KLIP-1 antibody, 1:5000 in PBS, 0.2% Tween 20. After washing, the blots were incubated with horseradish peroxidase-conjugated goat anti-rabbit antibodies; the coloration is obtained using an ECL system (Amersham, Les Ulis, France), in accordance with the manufacturer's recommendations. The results given in FIG. 5 show the presence of the band for the KLIP molecule at 38 kDa in the KLIP+ umbilical cord cell fraction.

In Vitro Transcription and Translation of the KLIP-1 Protein and Immunoprecipitation 1. Preparation of the Matrix The translated matrix comes from the PCR amplification of the KLIP-1 gene cDNA, obtained by reverse transcription (MMLV RT, Gibco BRL, France) of RNA (RNA NOW, Biogentex, France) from cord blood mononuclear cells. The PCR is carried out in a total volume of 100 µl under the following conditions:

300 nM of sense +T7 primer (5'-AgATCCTAATACGACTCACTATAgggAggAgggACATgg CCAACTAAgC-3') (SEQ ID NO:21) and 300 nM antisense or reverse primer (5' AAgAggAAggAAggggTAgg3') (SEQ ID NO:22).

PCR amplification over 35 cycles (thermocycler 9600, PERKIN ELMER), 94° C., 1 minute; 55° C., 1 minute; 72° C., 2 minutes. Final elongation at 72° C., 10 minutes. The amplification product was purified by centrifugation (500 g for 20 minutes) on MICROCON 100 (AMICON, USA), and then taken up in $H_2O$.

2. In Vitro Transcription and Translation

The in vitro transcription and translation of the matrix were carried out using:
- 1 µg of matrix
- 40 µl of TnT Quick Master Mix (Promega Biotech, France)
- 2 µl of 10 mCi/ml $^{35}$S-methionine (Amersham, France)
- $H_2O$, QS 50 µl The reagents are incubated for 90 minutes at 30° C.

3. Immunoprecipitation

5 µl of the translation product and 2 µl of the rabbit polyclonal anti-KLIP-1 antibody are incubated in 50 µl of 1×PBS for 1 hour at 4° C. with agitation.

60 µl of protein A-sepharose are added and the mixture is incubated on a wheel for 30 minutes at 4° C.

Washing is carried out with buffer: 0.1% NP 40, 20 mM Tris-HCl, pH 7.5, 150 mM NaCl and 0.05% sodium azide.

Figure 6:
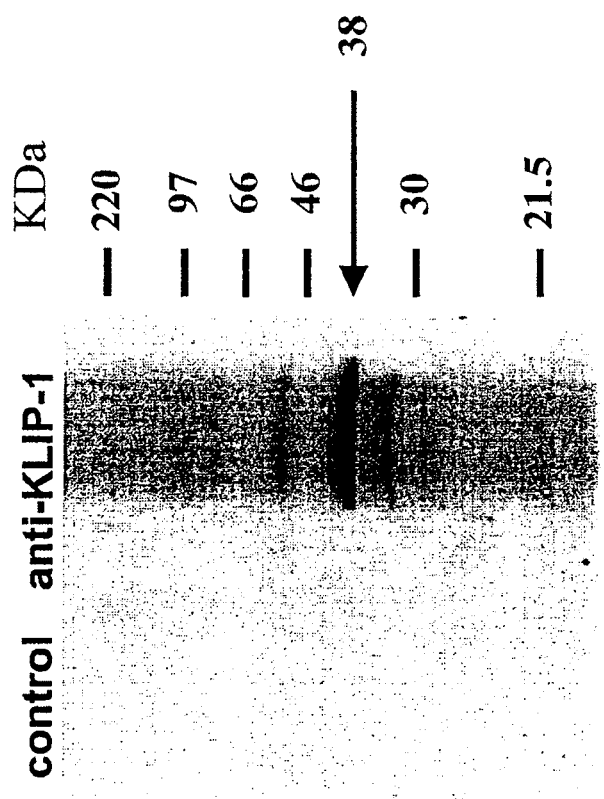
FIG. 6 illustrates an immunoprecipitation of the protein transcribed and translated in vitro.

The samples are analyzed by electrophoresis on an SDS-PAGE gel at 12%; the result is visualized by autoradiography. FIG. 6 shows the presence of a band, corresponding to the KLIP molecule, of approximately 38 kDa, detected with the anti-KLIP antibody, whereas the control pre-immune serum does not detect the KLIP protein. This shows the specificity of the anti-KLIP antibody.

Immunoselection of KLIP-1+ Cells

Approximately $2.5 \times 10^8$ mononuclear cells from peripheral or umbilical cord blood, from bone marrow or from thymus and from fetal liver are incubated in 20% human AB serum in PBS, for 30 minutes at room temperature. After washing in PBS containing 2% SVF, the cells are incubated with 90 µl of rabbit anti-KLIP-1 serum (in accordance with the invention) for 30 minutes at 4° C., then incubated with 50 µl of FITC-labeled anti-rabbit IgG anti-swine (Dako, France) for 30 minutes at 4° C., and then incubated with 200 µl of anti-FITC magnetic microbeads (Miltenyi-Biotech, Paris, France) for 30 minutes at 4° C.

The KLIP-1+ cells are subsequently isolated by successive passages over LS+ magnetic columns (Miltenyi-Biotech, Paris, France) and then RS+ magnetic columns in a magnetic field using the VarioMACS machine (Miltenyi-Biotech, Paris, France).

The resulting populations were analyzed by FACS-Vantage (Becton Dickinson, France) and the purity of the populations used in this study ranged between 90 and 99%.

Immunophenotyping by FACS

A 1-, 2-, and 3-color immunofluorescence analysis of the KLIP-1+ cell population was performed using a FACS-Vantage (Becton Dickinson, France).

Figure 7:
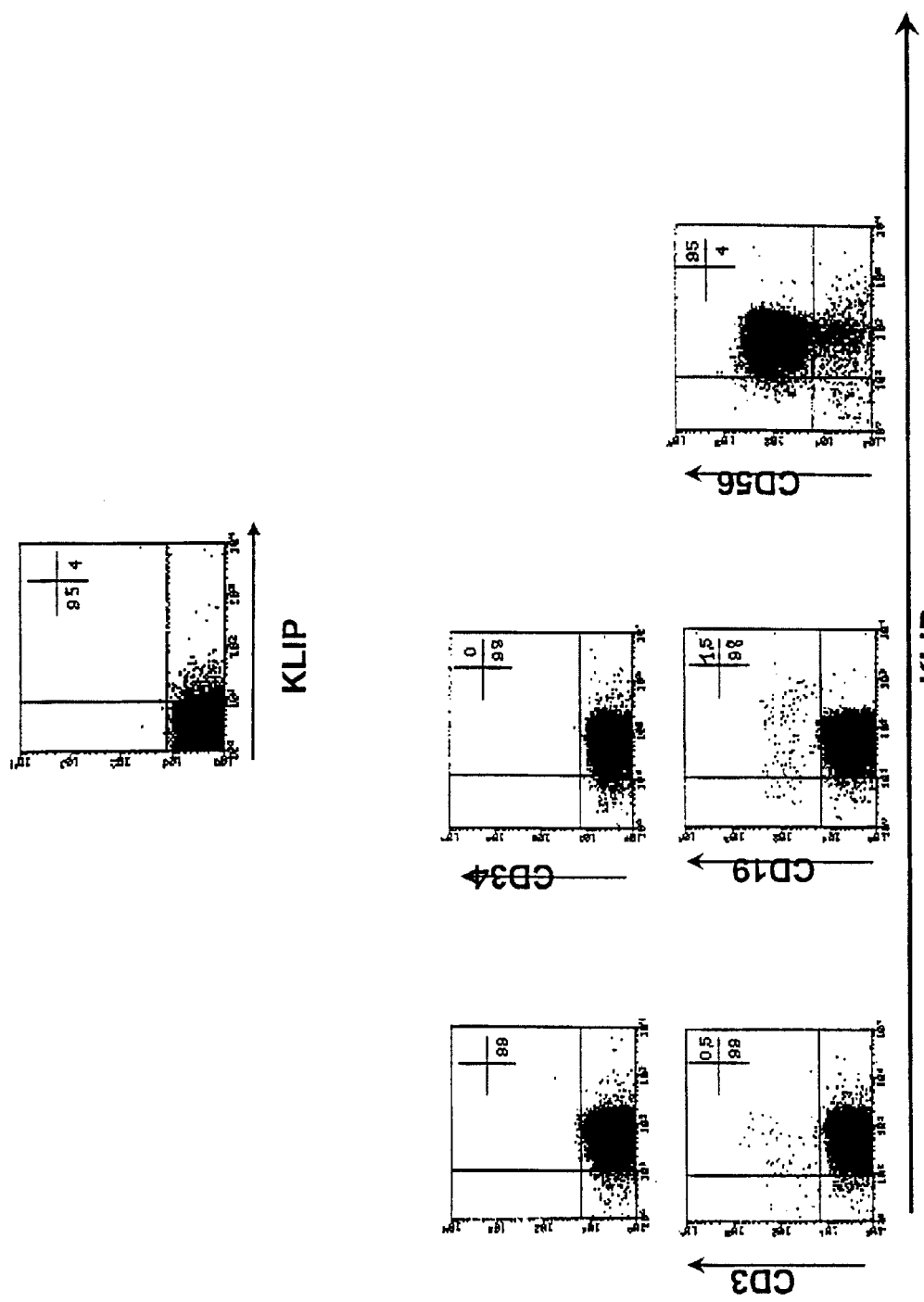
FIG. 7 represents the distribution of KLIP-1+ cells in peripheral blood, containing only mature blood cells.

Suitable conjugated fluorochromes, unrelated to the control Igs appropriate to the isotype, were also used in all the experiments. The results are given per hematopoietic tissue:

.FIGS. 7-11 (Human Cells):

FIG. 7: Peripheral Blood: Containing Only Mature Blood Cells

In total blood, 4% of the mononuclear cells are KLIP-1+. In the 99% pure KLIP-1+ sorted fraction, 0% CD34+, 95% CD56+ (mature NK cells), 1.5% CD19+ (B cells) and 0.5% CD3+ (T cells) are found, these last two values being due to the background noise.

Figure 8:
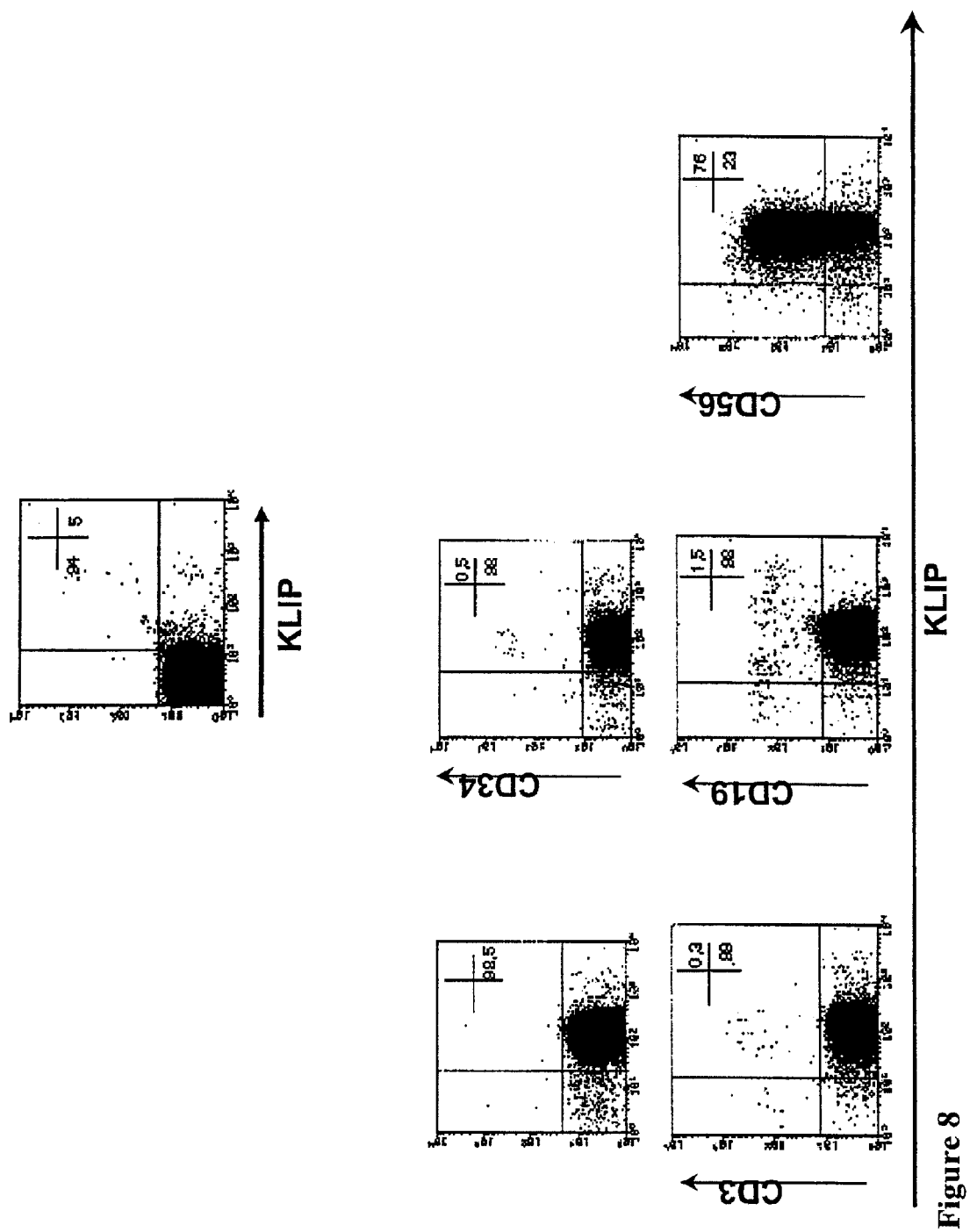
FIG. 8 represents the distribution of KLIP-1+ cells in umbilical cord blood, containing mostly mature blood cells but also a small fraction of immature cells.

FIG. 8: Umbilical Cord Blood, Contains Mostly Mature Blood Cells But Also a Small Fraction of Immature Cells In total cord blood, 5% of the mononuclear cells are KLIP-1+.

In the 98.5% pure KLIP-1+ sorted fraction, 0.5% CD34+, 76% CD56+ (mature NK cells), 1.5% CD19+ (B cells) and 0.3% CD3+ (T cells) are found.

Figure 9:
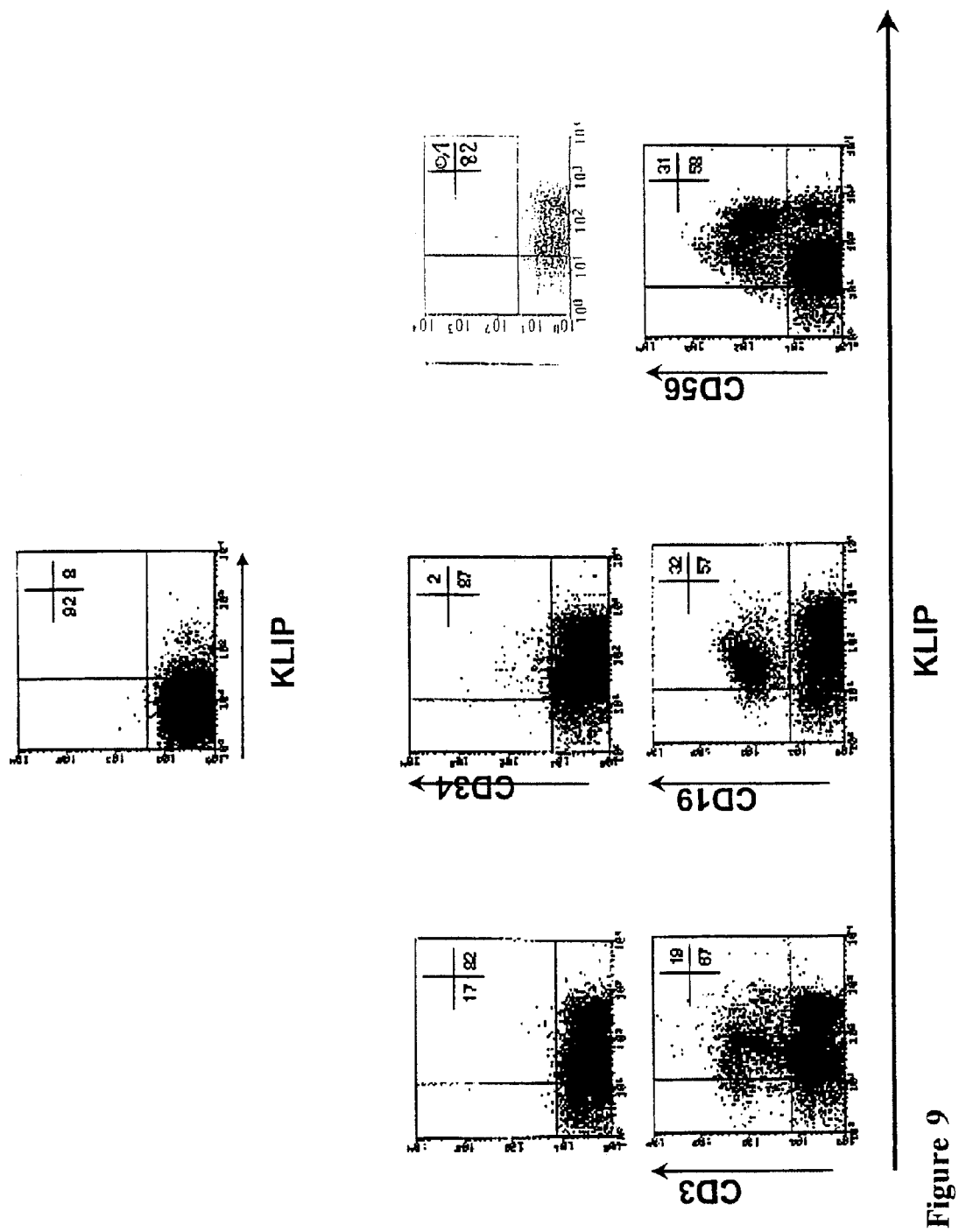
FIG. 9 represents the distribution of KLIP-1+ cells in the bone marrow, a site of hematopoiesis at which the differentiation of blood cells takes place.

FIG. 9: Bone Marrow: Site of Hematopoiesis at which Blood Cell Differentiation Takes Place; it Therefore Contains all the Immature Blood Cells In total bone marrow, 8% of the mononuclear cells are KLIP-1+.

In the 99% pure KLIP-1+ sorted fraction, two subpopulations "low intensity and high intensity" namely 17% KLIP-1 low +82% KLIP-1 high +, and 32% CD19 KLIP-1 low (B cells), 19% CD3 KLIP-1 low (pre-T cells), 31% CD56+KLIP-1 high + (NK), are found.

Figure 10:
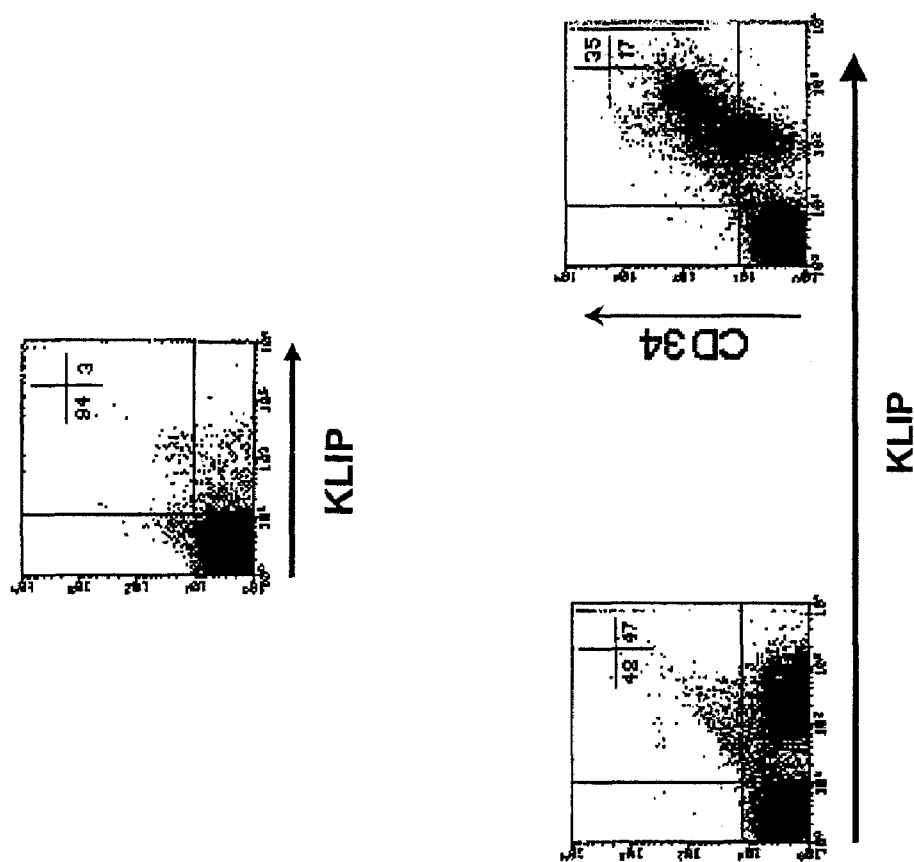
FIG. 10 represents the distribution of KLIP-1+ cells in embryonic liver (6 weeks)

FIG. 10: Embryonic Liver (6 Weeks)

In the mononuclear cells of total liver, 3% of the cells are KLIP-1+.

Since few cells are obtained, yield was favored over purity.

Of the 47% of KLIP-1+cells, 35% are CD34+ (very early hematopoietic progenitors).

Figure 11:
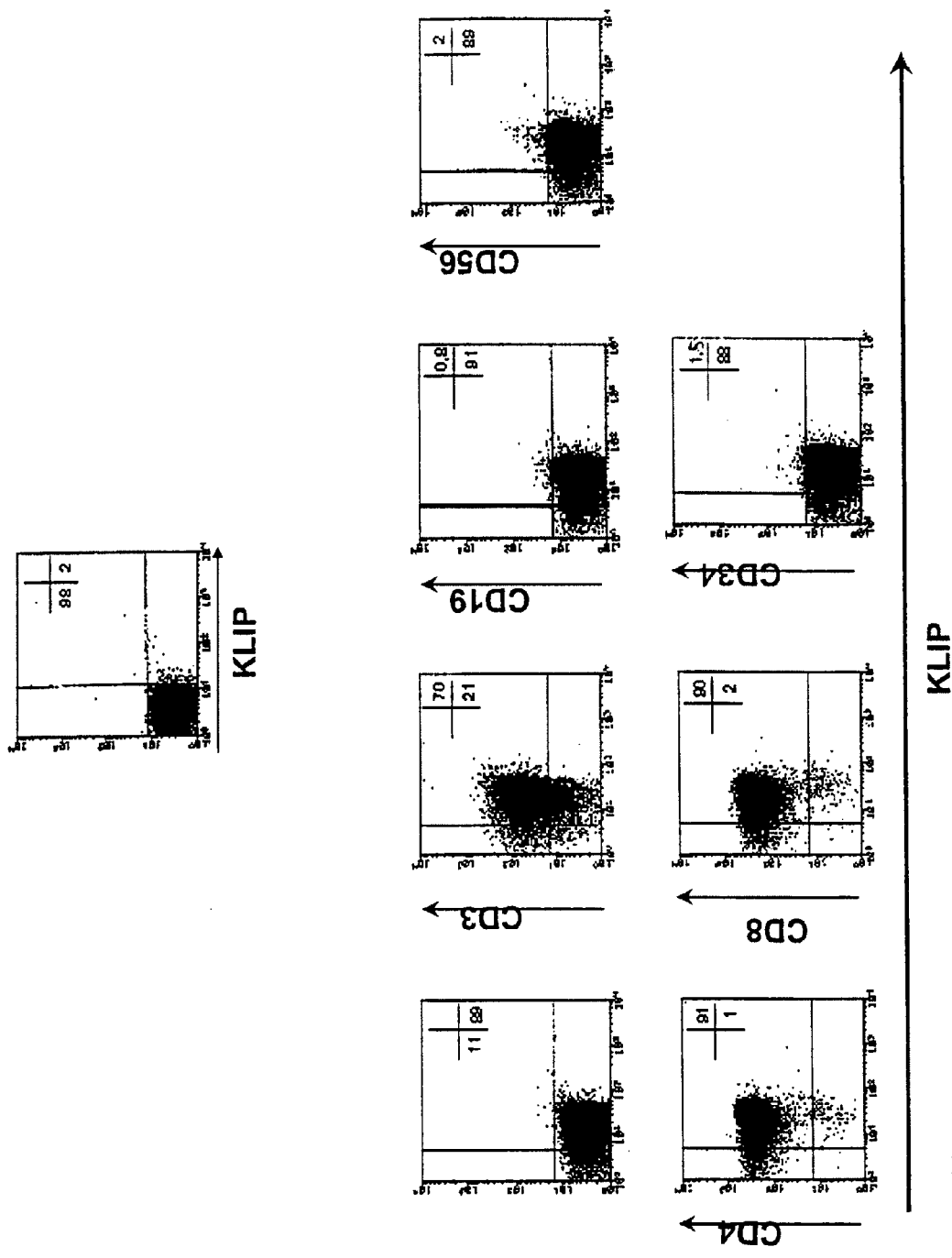
FIG. 11 represents the distribution of KLIP-1+ cells in neonatal thymus.

FIG. 11: Neonatal Thymus

The thymus is an organ for immunological maturation of T cells.

In total thymus, 2% of the mononuclear cells are KLIP-1+.

In the 98% pure KLIP-1+ sorted fraction, 1.5% CD34+, 2% CD56+, 0.8% CD19+ (B cells) and 70% CD3+ (T cells or, at this maturation stage, T/NK cells) are found. However, the KLIP-1+CD3+ population is made up of more than 91% CD4+ CD8+ (pre-T) cells.

These results clearly show that the KLIP-1 marker (antigen or molecule) is specifically present on NK cells throughout their hematopoietic differentiation, since it is present on the CD34+ early progenitors of the marrow and cord. It is always present on CD56− immature NK cells and CD56+ mature NK cells and on immature pre-B and pre-T cells. In neonatal thymus, the presence of the KLIP antigen is observed on CD3+CD4+CD8+ cells, which are immature T cells, since mature T cells, which are CD3+CD4−CD8+ or CD3+CD4+CD8−, are KLIP-1−.

Figure 13:
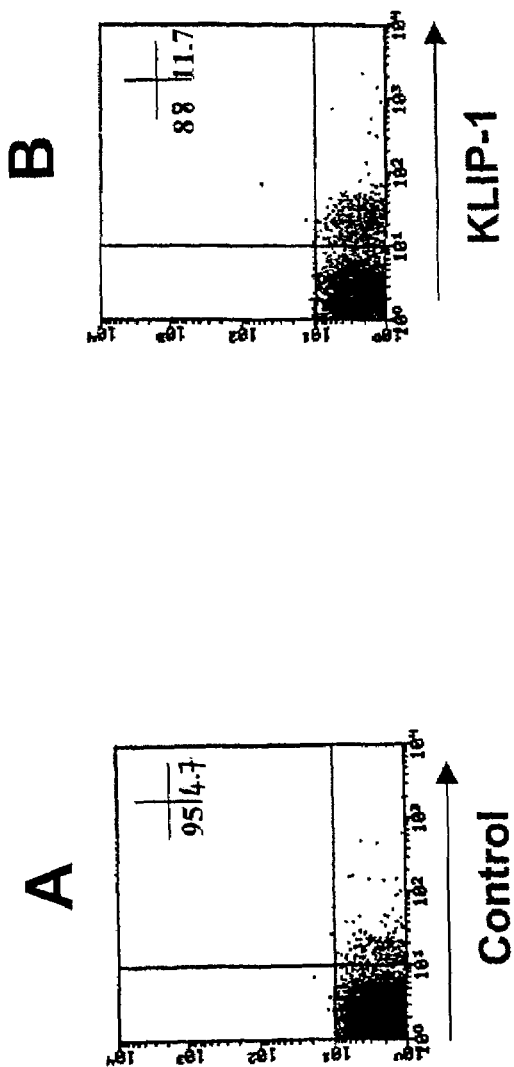
FIG. 13 illustrates the distribution of KLIP-1+ cells in the peripheral blood of pigs.
Figure 14:
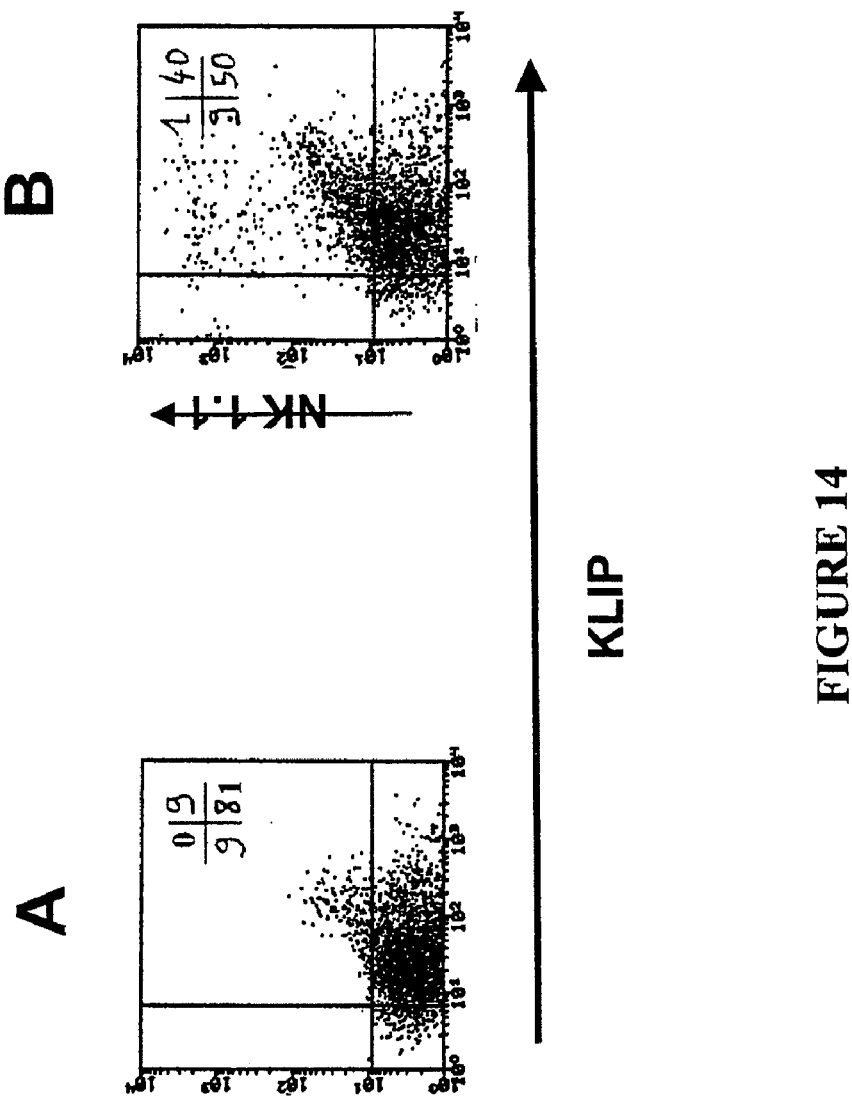
FIG. 14 illustrates the distribution of KLIP-1+ cells in mouse splenocytes considered to be NK cells (formation of complexes with NK 1.1 antibodies (Pharmingen)).

.FIGS. 13-14 (Animal Cells)

FIG. 13 (pigs): in total blood, 7% of the mononuclear cells are KLIP-1+: difference between the negative control (FIG. 13A), obtained by incubating pig total blood with a nonimmunized rabbit serum, and the positive control, obtained with an immunized rabbit serum.

FIG. 14 (mice): FIG. 14A: in the KLIP-1+ sorted fraction: 98% purity (9% background noise); FIG. 14B: in the presence of anti-murine NK cell antibodies (NK1.1), it is noted that 40% of the KLIP-1+ cells are NK cells.

Cell-Mediated Cytotoxicity

Spontaneous cytotoxicity and antibody-dependent cell-mediated cytotoxicity (ADCC) were measured in a standard 4-hour $^{51}$Cr radioisotope-release experiment. NK-sensitive K562 erythroleukemia cells (American Type Culture Collection, Rockville, Md.) were used as the target. The targeted cells were labeled with 200 µCi of $^{51}$Cr-sodium chromate (Amersham, Les Ulis, France) for 2 h. A varying number of effector cells, not mixed and originating from various donors (<50 years old), in 100 µl, were added to the target cells and incubated for 4 h at 37° C. To measure the ADCC, the cells were preincubated with the pig anti-rabbit anti-Fc receptor, 1:50. All determinations were made in triplicate.

Figure 12:
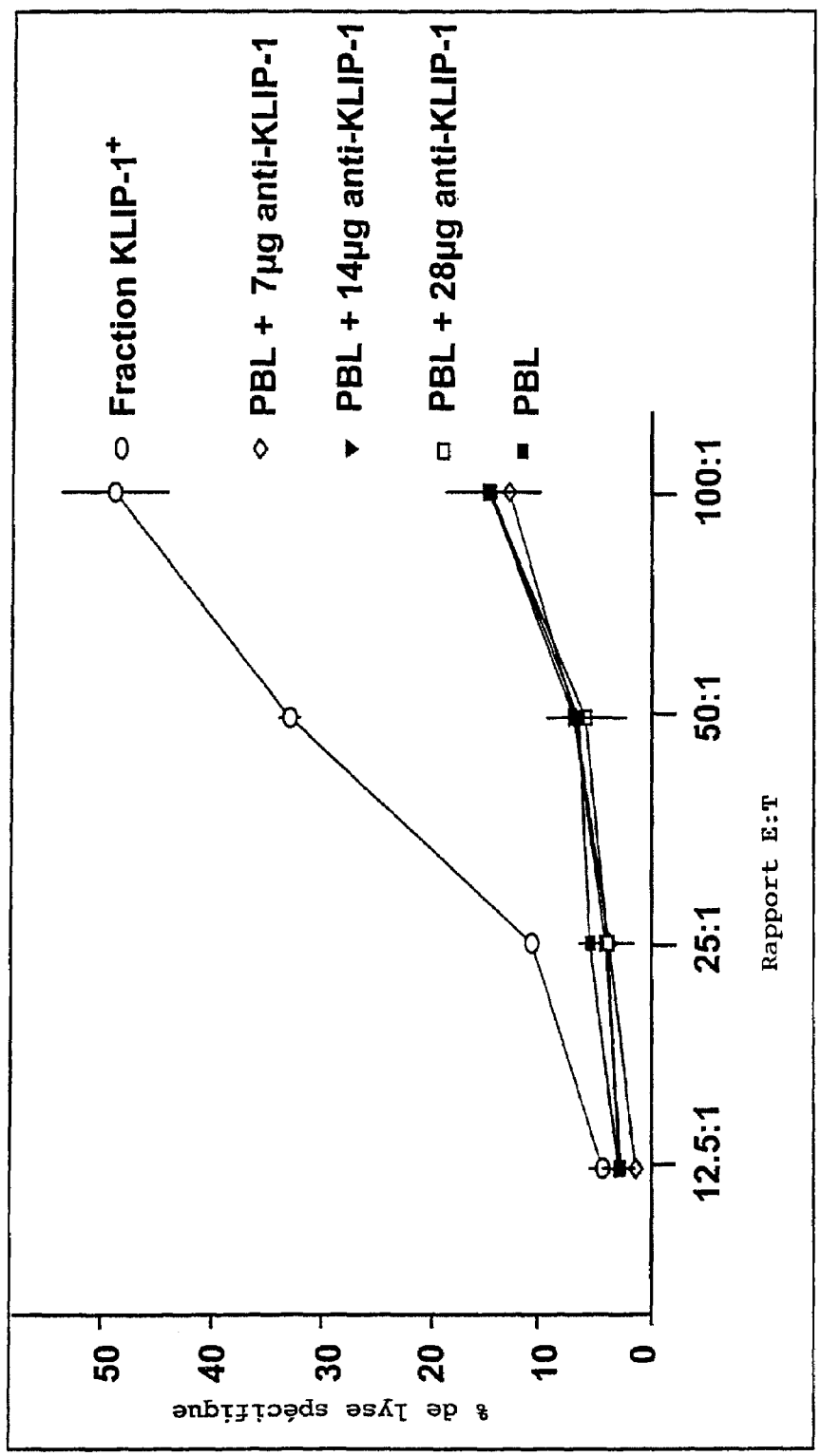
FIG. 12 illustrates the cytolytic properties of NK cells and of the NK population purified with KLIP-1+ (target cells)

The results obtained, given in FIG. 12, show that:
1. the anti-KLIP-1 antibody has no effect on the cytotoxicity of the NK cells, and therefore the KLIP antigen is neither an inhibitor nor an activator of NKs;
2. sorting (separation or selection) of the KLIP-1+ cells increases the cytotoxicity, probably due to a concentration effect, and this nevertheless proves that the cells in the peripheral blood which are sorted by anti-KLIP-1 are indeed NK cells with cytotoxic functions.

As emerges from the above, the invention is in no way limited to its methods of implementation, preparation and application which have just been described more explicitly; on the contrary, it encompasses all the variants thereof which may occur to a person skilled in the art, without departing from the context or the scope of the present invention.

---

The invention claimed is:

1. An isolated human cell surface protein wherein said protein:
   consists of SEQ ID NO:25,
   is derived from a human precursor of the sequence SEQ ID NO:2 that comprises a 20 amino acid N-terminal signal sequence,
   is expressed at the surface of human lymphoid progenitor cells and mature NK cells,
   has an apparent molecular weight of approximately 36-38 kDa, and
   has a structure comprising an extracellular domain, five transmembrane domains and a cytoplasmic domain, located, respectively, between positions 21 and 152, 153 and 295, and 296 and 350, with reference to the sequence SEQ ID NO:2.

2. An isolated fragment of the protein according to claim 1, consisting of SEQ ID NO: 7.

3. An isolated precursor of a human cell surface protein consisting of SEQ ID NO:2.

* * * * *

SEQUENCE LISTING

<160> NUMBER OF SEQ ID NOS: 25

<210> SEQ ID NO 1
<211> LENGTH: 1501
<212> TYPE: DNA
<213> ORGANISM: Homo sapiens
<220> FEATURE:
<221> NAME/KEY: CDS
<222> LOCATION: (116)...(1168)

<400> SEQUENCE: 1

```
cgcggccgcg tcgacctctc ctcgaccctg gacgtctacc ttccggaggc ccacatcttg      60
cccactccgc gcgcggggct agcgcgggtt tcagcgacgg gagccctcaa gggac atg     118
                                                                Met
                                                                  1 gca act aca gcg gcg ccg gcg ggc ggc gcc cga aat gga gct ggc ccg      166
Ala Thr Thr Ala Ala Pro Ala Gly Gly Ala Arg Asn Gly Ala Gly Pro
          5                  10                  15 gaa tgg gga ggg ttc gaa gaa aac atc cag ggc gga ggc tca gct gtg      214
Glu Trp Gly Gly Phe Glu Glu Asn Ile Gln Gly Gly Gly Ser Ala Val
         20                  25                  30 att gac atg gag aac atg gat gat acc tca ggc tct agc ttc gag gat      262
Ile Asp Met Glu Asn Met Asp Asp Thr Ser Gly Ser Ser Phe Glu Asp
     35                  40                  45 atg ggt gag ctg cat cag cgc ctg cgc gag gaa gaa gta gac gct gat      310
Met Gly Glu Leu His Gln Arg Leu Arg Glu Glu Glu Val Asp Ala Asp
 50                  55                  60                  65 gca gct gat gca gct gct gct gaa gag gag gat gga gag ttc ctg ggc      358
Ala Ala Asp Ala Ala Ala Ala Glu Glu Glu Asp Gly Glu Phe Leu Gly
                 70                  75                  80 atg aag ggc ttt aag gga cag ctg agc cgg cag gtg gca gat cag atg      406
Met Lys Gly Phe Lys Gly Gln Leu Ser Arg Gln Val Ala Asp Gln Met
             85                  90                  95 tgg cag gct ggg aaa aga caa gcc tcc agg gcc ttc agc ttg tac gcc      454
Trp Gln Ala Gly Lys Arg Gln Ala Ser Arg Ala Phe Ser Leu Tyr Ala
            100                 105                 110 aac atc gac atc ctc aga ccc tac ttt gat gtg gag cct gct cag gtg      502
Asn Ile Asp Ile Leu Arg Pro Tyr Phe Asp Val Glu Pro Ala Gln Val
        115                 120                 125 cga agc agg ctc ctg gag tcc atg atc cct atc aag atg gtc aac ttc      550
Arg Ser Arg Leu Leu Glu Ser Met Ile Pro Ile Lys Met Val Asn Phe
130                 135                 140                 145 ccc cag aaa att gca ggt gaa ctc tat gga cct ctc atg ctg gtc ctc      598
Pro Gln Lys Ile Ala Gly Glu Leu Tyr Gly Pro Leu Met Leu Val Leu
                150                 155                 160 act ctg gtt gct atc cta ctc cat ggg atg aag acg tct gac act att      646
Thr Leu Val Ala Ile Leu Leu His Gly Met Lys Thr Ser Asp Thr Ile
            165                 170                 175 atc cgg gag ggc acc ctg atg ggc aca gcc att ggc acc tgc ttc ggc      694
Ile Arg Glu Gly Thr Leu Met Gly Thr Ala Ile Gly Thr Cys Phe Gly
        180                 185                 190 tac tgg ctg gga gtc tcc tcc ttc att tac ttc ctt gcc tac ctg tgc      742
Tyr Trp Leu Gly Val Ser Ser Phe Ile Tyr Phe Leu Ala Tyr Leu Cys
    195                 200                 205
```

-continued

| | | |
|---|---|---|
| aac gcc cag atc acc atg ctg cag atg ttg gca ctg ctg ggc tat ggc<br>Asn Ala Gln Ile Thr Met Leu Gln Met Leu Ala Leu Leu Gly Tyr Gly<br>210                   215                   220                   225 | 790 |
| ctc ttt ggg cat tgc att gtc ctg ttc atc acc tat aat atc cac ctc<br>Leu Phe Gly His Cys Ile Val Leu Phe Ile Thr Tyr Asn Ile His Leu<br>                      230                   235                   240 | 838 |
| cac gcc ctc ttc tac ctc ttc tgg ctg ttg gtg ggt gga ctg tcc aca<br>His Ala Leu Phe Tyr Leu Phe Trp Leu Leu Val Gly Gly Leu Ser Thr<br>                  245                   250                   255 | 886 |
| ctg cgc atg gta gca gtg ttg gtg tct cgg acc gtg ggc ccc aca cag<br>Leu Arg Met Val Ala Val Leu Val Ser Arg Thr Val Gly Pro Thr Gln<br>            260                   265                   270 | 934 |
| cgg ctg ctc ctc tgt ggc acc ctg gct gcc cta cac atg ctc ttc ctg<br>Arg Leu Leu Leu Cys Gly Thr Leu Ala Ala Leu His Met Leu Phe Leu<br>275                   280                   285 | 982 |
| ctc tat ctg cat ttt gcc tac cac aaa gtg gta gag ggg atc ctg gac<br>Leu Tyr Leu His Phe Ala Tyr His Lys Val Val Glu Gly Ile Leu Asp<br>290                   295                   300                   305 | 1030 |
| aca ctg gag ggc ccc aac atc ccg ccc atc cag agg gtc ccc aga gac<br>Thr Leu Glu Gly Pro Asn Ile Pro Pro Ile Gln Arg Val Pro Arg Asp<br>                      310                   315                   320 | 1078 |
| atc cct gcc atg ctc cct gct gct cgg ctt ccc acc acc gtc ctc aac<br>Ile Pro Ala Met Leu Pro Ala Ala Arg Leu Pro Thr Thr Val Leu Asn<br>                  325                   330                   335 | 1126 |
| gcc aca gcc aaa gct gtt gcg gtg acc ctg cag tca cac tga<br>Ala Thr Ala Lys Ala Val Ala Val Thr Leu Gln Ser His *<br>340                   345                   350 | 1168 |
| ccccacctga aattcttggc cagtcctctt tcccgcagct gcagagagga ggaagactat | 1228 |
| taaaggacag tcctgatgac atgtttcgta gatggggttt gcagctgcca ctgagctgta | 1288 |
| gctgcgtaag tacctccttg atgcctgtgg gcacttctga aaggcacaag gccaagaact | 1348 |
| cctggccagg actgcaaggc tctgcagcca atgcagaaaa tgggtcaggt cctttgagaa | 1408 |
| cccctcccca cctaccccctt ccttcctctt tatctctccc acattgtctt ggtaaatata | 1468 |
| gacttggtaa ttaaaatgtt gattgaagtc tgg | 1501 |

<210> SEQ ID NO 2
<211> LENGTH: 350
<212> TYPE: PRT
<213> ORGANISM: Homo sapiens

<400> SEQUENCE: 2

Met Ala Thr Thr Ala Ala Pro Ala Gly Gly Ala Arg Asn Gly Ala Gly
1                  5                   10                   15

Pro Glu Trp Gly Gly Phe Glu Glu Asn Ile Gln Gly Gly Gly Ser Ala
                 20                   25                   30

Val Ile Asp Met Glu Asn Met Asp Asp Thr Ser Gly Ser Ser Phe Glu
            35                   40                   45

Asp Met Gly Glu Leu His Gln Arg Leu Arg Glu Glu Val Asp Ala
Asp          50                   55                   60

Asp Ala Ala Asp Ala Ala Ala Glu Glu Asp Gly Glu Phe Leu
65                   70                   75                   80

Gly Met Lys Gly Phe Lys Gly Gln Leu Ser Arg Gln Val Ala Asp Gln
                 85                   90                   95

Met Trp Gln Ala Gly Lys Arg Gln Ala Ser Arg Ala Phe Ser Leu Tyr
                 100                 105               110

Ala Asn Ile Asp Ile Leu Arg Pro Tyr Phe Asp Val Glu Pro Ala Gln
            115                 120               125

```
Val Arg Ser Arg Leu Leu Glu Ser Met Ile Pro Ile Lys Met Val Asn
    130                 135                 140
Phe Pro Gln Lys Ile Ala Gly Glu Leu Tyr Gly Pro Leu Met Leu Val
145                 150                 155                 160
Leu Thr Leu Val Ala Ile Leu Leu His Gly Met Lys Thr Ser Asp Thr
                165                 170                 175
Ile Ile Arg Glu Gly Thr Leu Met Gly Thr Ala Ile Gly Thr Cys Phe
            180                 185                 190
Gly Tyr Trp Leu Gly Val Ser Ser Phe Ile Tyr Phe Leu Ala Tyr Leu
        195                 200                 205
Cys Asn Ala Gln Ile Thr Met Leu Gln Met Leu Ala Leu Leu Gly Tyr
    210                 215                 220
Gly Leu Phe Gly His Cys Ile Val Leu Phe Ile Thr Tyr Asn Ile His
225                 230                 235                 240
Leu His Ala Leu Phe Tyr Leu Phe Trp Leu Leu Val Gly Gly Leu Ser
                245                 250                 255
Thr Leu Arg Met Val Ala Val Leu Val Ser Arg Thr Val Gly Pro Thr
            260                 265                 270
Gln Arg Leu Leu Leu Cys Gly Thr Leu Ala Ala Leu His Met Leu Phe
        275                 280                 285
Leu Leu Tyr Leu His Phe Ala Tyr His Lys Val Val Glu Gly Ile Leu
    290                 295                 300
Asp Thr Leu Glu Gly Pro Asn Ile Pro Pro Ile Gln Arg Val Pro Arg
305                 310                 315                 320
Asp Ile Pro Ala Met Leu Pro Ala Ala Arg Leu Pro Thr Thr Val Leu
                325                 330                 335
Asn Ala Thr Ala Lys Ala Val Ala Val Thr Leu Gln Ser His
            340                 345                 350

<210> SEQ ID NO 3
<211> LENGTH: 507
<212> TYPE: DNA
<213> ORGANISM: Mus musculus
<220> FEATURE:
<221> NAME/KEY: CDS
<222> LOCATION: (1)...(507)

<400> SEQUENCE: 3 aac atc cag ggc ggg ggt tcg gct gtg att gat atg gag aac atg gac    48
Asn Ile Gln Gly Gly Gly Ser Ala Val Ile Asp Met Glu Asn Met Asp
  1               5                  10                  15 gat acc tca ggc tcc agc ttc gag gac atg ggt gag ctg cac cag cgc    96
Asp Thr Ser Gly Ser Ser Phe Glu Asp Met Gly Glu Leu His Gln Arg
             20                  25                  30 ctg cgg gag gaa gaa gta gat gct gat gca gct gct gca gaa gaa gag   144
Leu Arg Glu Glu Glu Val Asp Ala Asp Ala Ala Ala Ala Glu Glu Glu
         35                  40                  45 gat ggg gag ttt ctt ggc atg aaa ggc ttt aaa gga caa ctg agc cgg   192
Asp Gly Glu Phe Leu Gly Met Lys Gly Phe Lys Gly Gln Leu Ser Arg
     50                  55                  60 cag gta gca gat cag atg tgg cag gca ggg aag aga cag gct tcc agg   240
Gln Val Ala Asp Gln Met Trp Gln Ala Gly Lys Arg Gln Ala Ser Arg
 65                  70                  75                  80 gcc ttc agc ttg tat gcc aac att gac atc ctc aga ccc tac ttt gat   288
Ala Phe Ser Leu Tyr Ala Asn Ile Asp Ile Leu Arg Pro Tyr Phe Asp
                 85                  90                  95 gtg gag cct gcc cag gtc cga agc agg ctc ctg gag tcc atg atc cct   336
```

```
Val Glu Pro Ala Gln Val Arg Ser Arg Leu Leu Glu Ser Met Ile Pro
            100                 105                 110 atc aag atg gtc aac ttc ccc cag aaa gtc gcg ggc gag ctc tac gga      384
Ile Lys Met Val Asn Phe Pro Gln Lys Val Ala Gly Glu Leu Tyr Gly
        115                 120                 125 ccg ctc atg ctg gtc ttc aca ctg gtg gcc atc ctc ctg cat gga atg      432
Pro Leu Met Leu Val Phe Thr Leu Val Ala Ile Leu Leu His Gly Met
    130                 135                 140 aag act tct gac acc att atc cgg gag ggc acc ctc atg ggc aca gcc      480
Lys Thr Ser Asp Thr Ile Ile Arg Glu Gly Thr Leu Met Gly Thr Ala
145                 150                 155                 160 ata ggc acc tgc ttt gga tac tgg ctg                                  507
Ile Gly Thr Cys Phe Gly Tyr Trp Leu
                165
```

<210> SEQ ID NO 4
<211> LENGTH: 169
<212> TYPE: PRT
<213> ORGANISM: Mus musculus

<400> SEQUENCE: 4

```
Asn Ile Gln Gly Gly Gly Ser Ala Val Ile Asp Met Glu Asn Met Asp
 1               5                  10                  15

Asp Thr Ser Gly Ser Ser Phe Glu Asp Met Gly Glu Leu His Gln Arg
            20                  25                  30

Leu Arg Glu Glu Glu Val Asp Ala Asp Ala Ala Ala Glu Glu Glu
        35                  40                  45

Asp Gly Glu Phe Leu Gly Met Lys Gly Phe Lys Gly Gln Leu Ser Arg
    50                  55                  60

Gln Val Ala Asp Gln Met Trp Gln Ala Gly Lys Arg Gln Ala Ser Arg
65                  70                  75                  80

Ala Phe Ser Leu Tyr Ala Asn Ile Asp Ile Leu Arg Pro Tyr Phe Asp
                85                  90                  95

Val Glu Pro Ala Gln Val Arg Ser Arg Leu Leu Glu Ser Met Ile Pro
            100                 105                 110

Ile Lys Met Val Asn Phe Pro Gln Lys Val Ala Gly Glu Leu Tyr Gly
        115                 120                 125

Pro Leu Met Leu Val Phe Thr Leu Val Ala Ile Leu Leu His Gly Met
    130                 135                 140

Lys Thr Ser Asp Thr Ile Ile Arg Glu Gly Thr Leu Met Gly Thr Ala
145                 150                 155                 160

Ile Gly Thr Cys Phe Gly Tyr Trp Leu
                165
```

<210> SEQ ID NO 5
<211> LENGTH: 471
<212> TYPE: DNA
<213> ORGANISM: Sus sp.
<220> FEATURE:
<221> NAME/KEY: CDS
<222> LOCATION: (1)...(471)
<220> FEATURE:
<221> NAME/KEY: misc_feature
<222> LOCATION: (1)...(60)
<223> OTHER INFORMATION: Signal peptide 1-60
<220> FEATURE:
<221> NAME/KEY: misc_feature
<222> LOCATION: (61)...(456)

<400> SEQUENCE: 5

```
atg gca act aca gcg gcg ccg gcg ggc ggc gcc cga aat gga gct ggc       48
```

```
Met Ala Thr Thr Ala Ala Pro Ala Gly Gly Ala Arg Asn Gly Ala Gly
1               5                   10                  15 ccg gaa tgg gga ggg ttc gaa gaa aac atc cag ggc gga ggc tca gct    96
Pro Glu Trp Gly Gly Phe Glu Glu Asn Ile Gln Gly Gly Gly Ser Ala
            20                  25                  30 gtg att gac atg gag aac atg gat gat acc tca ggc tct agc ttc gag   144
Val Ile Asp Met Glu Asn Met Asp Asp Thr Ser Gly Ser Ser Phe Glu
        35                  40                  45 gat atg ggt gag ctg cat cag cgc ctg cgc gag gaa gaa gta gac gct   192
Asp Met Gly Glu Leu His Gln Arg Leu Arg Glu Glu Glu Val Asp Ala
    50                  55                  60 gat gca gct gat gca gct gct gct gaa gag gag gat gga gag ttc ctg   240
Asp Ala Ala Asp Ala Ala Ala Ala Glu Glu Glu Asp Gly Glu Phe Leu
65              70                  75                  80 ggc atg aag ggc ttt aag gga cag ctg agc cgg cag gtg gca gat cag   288
Gly Met Lys Gly Phe Lys Gly Gln Leu Ser Arg Gln Val Ala Asp Gln
                85                  90                  95 atg tgg cag gct ggg aaa aga caa gcc tcc agg gcc ttc agc ttg tac   336
Met Trp Gln Ala Gly Lys Arg Gln Ala Ser Arg Ala Phe Ser Leu Tyr
            100                 105                 110 gcc aac atc gac atc ctc aga ccc tac ttt gat gtg gag cct gct cag   384
Ala Asn Ile Asp Ile Leu Arg Pro Tyr Phe Asp Val Glu Pro Ala Gln
        115                 120                 125 gtg cga agc agg ctc ctg gag tcc atg atc cct atc aag atg gtc aac   432
Val Arg Ser Arg Leu Leu Glu Ser Met Ile Pro Ile Lys Met Val Asn
    130                 135                 140 ttc ccc cag aaa att gca ggt gaa ctc tat gga cct ctc                471
Phe Pro Gln Lys Ile Ala Gly Glu Leu Tyr Gly Pro Leu
145                 150                 155

<210> SEQ ID NO 6
<211> LENGTH: 157
<212> TYPE: PRT
<213> ORGANISM: Sus sp.

<400> SEQUENCE: 6

Met Ala Thr Thr Ala Ala Pro Ala Gly Gly Ala Arg Asn Gly Ala Gly
1               5                   10                  15

Pro Glu Trp Gly Gly Phe Glu Glu Asn Ile Gln Gly Gly Gly Ser Ala
            20                  25                  30

Val Ile Asp Met Glu Asn Met Asp Asp Thr Ser Gly Ser Ser Phe Glu
        35                  40                  45

Asp Met Gly Glu Leu His Gln Arg Leu Arg Glu Glu Glu Val Asp Ala
    50                  55                  60

Asp Ala Ala Asp Ala Ala Ala Ala Glu Glu Glu Asp Gly Glu Phe Leu
65              70                  75                  80

Gly Met Lys Gly Phe Lys Gly Gln Leu Ser Arg Gln Val Ala Asp Gln
                85                  90                  95

Met Trp Gln Ala Gly Lys Arg Gln Ala Ser Arg Ala Phe Ser Leu Tyr
            100                 105                 110

Ala Asn Ile Asp Ile Leu Arg Pro Tyr Phe Asp Val Glu Pro Ala Gln
        115                 120                 125

Val Arg Ser Arg Leu Leu Glu Ser Met Ile Pro Ile Lys Met Val Asn
    130                 135                 140

Phe Pro Gln Lys Ile Ala Gly Glu Leu Tyr Gly Pro Leu
145                 150                 155

<210> SEQ ID NO 7
```

```
<211> LENGTH: 132
<212> TYPE: PRT
<213> ORGANISM: Homo sapiens

<400> SEQUENCE: 7

Gly Phe Glu Glu Asn Ile Gln Gly Gly Ser Ala Val Ile Asp Met
 1               5                  10                  15

Glu Asn Met Asp Asp Thr Ser Gly Ser Ser Phe Glu Asp Met Gly Glu
                20                  25                  30

Leu His Gln Arg Leu Arg Glu Glu Val Asp Ala Asp Ala Asp
                35                  40                  45

Ala Ala Ala Glu Glu Glu Asp Gly Glu Phe Leu Gly Met Lys Gly
        50                  55                  60

Phe Lys Gly Gln Leu Ser Arg Gln Val Ala Asp Gln Met Trp Gln Ala
 65                  70                  75                  80

Gly Lys Arg Gln Ala Ser Arg Ala Phe Ser Leu Tyr Ala Asn Ile Asp
                85                  90                  95

Ile Leu Arg Pro Tyr Phe Asp Val Glu Pro Ala Gln Val Arg Ser Arg
                100                 105                 110

Leu Leu Glu Ser Met Ile Pro Ile Lys Met Val Asn Phe Pro Gln Lys
                115                 120                 125

Ile Ala Gly Glu
        130

<210> SEQ ID NO 8
<211> LENGTH: 143
<212> TYPE: PRT
<213> ORGANISM: Homo sapiens

<400> SEQUENCE: 8

Leu Tyr Gly Pro Leu Met Leu Val Leu Thr Leu Val Ala Ile Leu Leu
 1               5                  10                  15

His Gly Met Lys Thr Ser Asp Thr Ile Ile Arg Glu Gly Thr Leu Met
                20                  25                  30

Gly Thr Ala Ile Gly Thr Cys Phe Gly Tyr Trp Leu Gly Val Ser Ser
        35                  40                  45

Phe Ile Tyr Phe Leu Ala Tyr Leu Cys Asn Ala Gln Ile Thr Met Leu
 50                  55                  60

Gln Met Leu Ala Leu Leu Gly Tyr Gly Leu Phe Gly His Cys Ile Val
 65                  70                  75                  80

Leu Phe Ile Thr Tyr Asn Ile His Leu His Ala Leu Phe Tyr Leu Phe
                85                  90                  95

Trp Leu Leu Val Gly Gly Leu Ser Thr Leu Arg Met Val Ala Val Leu
                100                 105                 110

Val Ser Arg Thr Val Gly Pro Thr Gln Arg Leu Leu Leu Cys Gly Thr
                115                 120                 125

Leu Ala Ala Leu His Met Leu Phe Leu Leu Tyr Leu His Phe Ala
        130                 135                 140

<210> SEQ ID NO 9
<211> LENGTH: 55
<212> TYPE: PRT
<213> ORGANISM: Homo sapiens

<400> SEQUENCE: 9

Tyr His Lys Val Val Glu Gly Ile Leu Asp Thr Leu Glu Gly Pro Asn
 1               5                  10                  15
```

Ile Pro Pro Ile Gln Arg Val Pro Arg Asp Ile Pro Ala Met Leu Pro
        20                  25                  30

Ala Ala Arg Leu Pro Thr Thr Val Leu Asn Ala Thr Ala Lys Ala Val
            35                  40                  45

Ala Val Thr Leu Gln Ser His
    50                  55

<210> SEQ ID NO 10
<211> LENGTH: 1053
<212> TYPE: DNA
<213> ORGANISM: Homo sapiens

<400> SEQUENCE: 10

| | | | | | | |
|---|---|---|---|---|---|---|
| atggcaacta | cagcggcgcc | ggcgggcggc | gcccgaaatg | gagctggccc | ggaatgggga | 60 |
| gggttcgaag | aaaacatcca | ggcggaggc | tcagctgtga | ttgacatgga | aacatggat | 120 |
| gatacctcag | gctctagctt | cgaggatatg | ggtgagctgc | atcagcgcct | gcgcgaggaa | 180 |
| gaagtagacg | ctgatgcagc | tgatgcagct | gctgctgaag | aggaggatgg | agagttcctg | 240 |
| ggcatgaagg | gctttaaggg | acagctgagc | cggcaggtgg | cagatcagat | gtggcaggct | 300 |
| gggaaaagac | aagcctccag | ggccttcagc | ttgtacgcca | acatcgacat | cctcagaccc | 360 |
| tactttgatg | tggagcctgc | tcaggtgcga | agcaggctcc | tggagtccat | gatccctatc | 420 |
| aagatggtca | acttccccca | gaaaattgca | ggtgaactct | atggacctct | catgctggtc | 480 |
| ctcactctgg | ttgctatcct | actccatggg | atgaagacgt | ctgacactat | tatccgggag | 540 |
| ggcaccctga | tgggcacagc | cattggcacc | tgcttcggct | actggctggg | agtctcatcc | 600 |
| ttcatttact | tccttgccta | cctgtgcaac | gcccagatca | ccatgctgca | gatgttggca | 660 |
| ctgctgggct | atggcctctt | tgggcattgc | attgtcctgt | tcatcaccta | taatatccac | 720 |
| ctccacgccc | tcttctacct | cttctggctg | ttggtgggtg | gactgtccac | actgcgcatg | 780 |
| gtagcagtgt | tggtgtctcg | gaccgtgggc | cccacacagc | ggctgctcct | ctgtggcacc | 840 |
| ctggctgccc | tacacatgct | cttcctgctc | tatctgcatt | ttgcctacca | caaagtggta | 900 |
| gaggggatcc | tggacacact | ggagggcccc | aacatcccgc | ccatccagag | ggtccccaga | 960 |
| gacatccctg | ccatgctccc | tgctgctcgg | cttcccacca | ccgtcctcaa | cgccacagcc | 1020 |
| aaagctgttg | cggtgaccct | gcagtcacac | tga | | | 1053 |

<210> SEQ ID NO 11
<211> LENGTH: 456
<212> TYPE: DNA
<213> ORGANISM: Homo sapiens

<400> SEQUENCE: 11

| | | | | | | |
|---|---|---|---|---|---|---|
| atggcaacta | cagcggcgcc | ggcgggcggc | gcccgaaatg | gagctggccc | ggaatgggga | 60 |
| gggttcgaag | aaaacatcca | ggcggaggc | tcagctgtga | ttgacatgga | aacatggat | 120 |
| gatacctcag | gctctagctt | cgaggatatg | ggtgagctgc | atcagcgcct | gcgcgaggaa | 180 |
| gaagtagacg | ctgatgcagc | tgatgcagct | gctgctgaag | aggaggatgg | agagttcctg | 240 |
| ggcatgaagg | gctttaaggg | acagctgagc | cggcaggtgg | cagatcagat | gtggcaggct | 300 |
| gggaaaagac | aagcctccag | ggccttcagc | ttgtacgcca | acatcgacat | cctcagaccc | 360 |
| tactttgatg | tggagcctgc | tcaggtgcga | agcaggctcc | tggagtccat | gatccctatc | 420 |
| aagatggtca | acttccccca | gaaaattgca | ggtgaa | | | 456 |

<210> SEQ ID NO 12

```
<211> LENGTH: 429
<212> TYPE: DNA
<213> ORGANISM: Homo sapiens

<400> SEQUENCE: 12
ctctatggac ctctcatgct ggtcctcact ctggttgcta tcctactcca tgggatgaag      60
acgtctgaca ctattatccg ggagggcacc ctgatgggca cagccattgg cacctgcttc     120
ggctactggc tgggagtctc atccttcatt tacttccttg cctacctgtg caacgcccag     180
atcaccatgc tgcagatgtt ggcactgctg gctatggcc tctttgggca ttgcattgtc      240
ctgttcatca cctataatat ccacctccac gccctcttct acctcttctg gctgttggtg     300
ggtggactgt ccacactgcg catggtagca gtgttggtgt ctcggaccgt gggccccaca     360
cagcggctgc tcctctgtgg caccctggct gccctacaca tgctcttcct gctctatctg     420
cattttgcc                                                             429

<210> SEQ ID NO 13
<211> LENGTH: 168
<212> TYPE: DNA
<213> ORGANISM: Homo sapiens

<400> SEQUENCE: 13
taccacaaag tggtagaggg gatcctggac acactggagg gccccaacat cccgcccatc      60
cagagggtcc ccagagacat ccctgccatg ctccctgctg ctcggcttcc caccaccgtc     120
ctcaacgcca cagccaaagc tgttgcggtg accctgcagt cacactga                  168

<210> SEQ ID NO 14
<211> LENGTH: 13
<212> TYPE: DNA
<213> ORGANISM: Homo sapiens

<400> SEQUENCE: 14
tttttttttt tgg                                                         13

<210> SEQ ID NO 15
<211> LENGTH: 10
<212> TYPE: DNA
<213> ORGANISM: Homo sapiens

<400> SEQUENCE: 15
gttgcgatcc                                                             10

<210> SEQ ID NO 16
<211> LENGTH: 20
<212> TYPE: DNA
<213> ORGANISM: Homo sapiens

<400> SEQUENCE: 16
accccacctg aaattcttgg                                                  20

<210> SEQ ID NO 17
<211> LENGTH: 20
<212> TYPE: DNA
<213> ORGANISM: Homo sapiens

<400> SEQUENCE: 17
gagataaaga ggaaggaagg                                                  20

<210> SEQ ID NO 18
<211> LENGTH: 20
```

-continued

```
<212> TYPE: DNA
<213> ORGANISM: Homo sapiens

<400> SEQUENCE: 18
ctgtgggcac ttctgaaagg                                                   20

<210> SEQ ID NO 19
<211> LENGTH: 20
<212> TYPE: DNA
<213> ORGANISM: Homo sapiens

<400> SEQUENCE: 19
tcgaagaaaa catccagggc                                                   20

<210> SEQ ID NO 20
<211> LENGTH: 21
<212> TYPE: DNA
<213> ORGANISM: Homo sapiens

<400> SEQUENCE: 20
agaggtccat agagttccac c                                                 21

<210> SEQ ID NO 21
<211> LENGTH: 49
<212> TYPE: DNA
<213> ORGANISM: Homo sapiens

<400> SEQUENCE: 21
agatcctaat acgactcact atagggagga gggacatggc caactaagc                   49

<210> SEQ ID NO 22
<211> LENGTH: 20
<212> TYPE: DNA
<213> ORGANISM: Homo sapiens

<400> SEQUENCE: 22
aagaggaagg aagggtagg                                                    20

<210> SEQ ID NO 23
<211> LENGTH: 387
<212> TYPE: DNA
<213> ORGANISM: Mus musculus
<220> FEATURE:
<221> NAME/KEY: CDS
<222> LOCATION: (1)...(387)

<400> SEQUENCE: 23 ggg ttc gaa gaa aac atc cag ggc ggg ggt tcg gct gtg att gat atg        48
Gly Phe Glu Glu Asn Ile Gln Gly Gly Gly Ser Ala Val Ile Asp Met
 1               5                  10                  15 gag aac atg gac gat acc tca ggc tcc agc ttc gag gac atg ggt gag        96
Glu Asn Met Asp Asp Thr Ser Gly Ser Ser Phe Glu Asp Met Gly Glu
             20                  25                  30 ctg cac cag cgc ctg cgg gag gaa gaa gta gat gct gat gca gct gct       144
Leu His Gln Arg Leu Arg Glu Glu Glu Val Asp Ala Asp Ala Ala Ala
         35                  40                  45 gca gaa gaa gag gat ggg gag ttt ctt ggc atg aaa ggc ttt aaa gga       192
Ala Glu Glu Glu Asp Gly Glu Phe Leu Gly Met Lys Gly Phe Lys Gly
     50                  55                  60 caa ctg agc cgg cag gta gca gat cag atg tgg cag gca ggg aag aga       240
Gln Leu Ser Arg Gln Val Ala Asp Gln Met Trp Gln Ala Gly Lys Arg
 65                  70                  75                  80 cag gct tcc agg gcc ttc agc ttg tat gcc aac att gac atc ctc aga       288
Gln Ala Ser Arg Ala Phe Ser Leu Tyr Ala Asn Ile Asp Ile Leu Arg
```

-continued

| | | | | | | | | | | | | | | | | |
|---|---|---|---|---|---|---|---|---|---|---|---|---|---|---|---|---|
|Gln|Ala|Ser|Arg|Ala|Phe|Ser|Leu|Tyr|Ala|Asn|Ile|Asp|Ile|Leu|Arg| |
| | | | |85| | | |90| | | |95| | | | |

```
ccc tac ttt gat gtg gag cct gcc cag gtc cga agc agg ctc ctg gag    336
Pro Tyr Phe Asp Val Glu Pro Ala Gln Val Arg Ser Arg Leu Leu Glu
        100                 105                 110 tcc atg atc cct atc aag atg gtc aac ttc ccc cag aaa gtc gcg ggc    384
Ser Met Ile Pro Ile Lys Met Val Asn Phe Pro Gln Lys Val Ala Gly
        115                 120                 125 gag                                                                 387
Glu
```

<210> SEQ ID NO 24
<211> LENGTH: 129
<212> TYPE: PRT
<213> ORGANISM: Mus musculus

<400> SEQUENCE: 24

Gly Phe Glu Glu Asn Ile Gln Gly Gly Ser Ala Val Ile Asp Met
1               5                   10                  15

Glu Asn Met Asp Asp Thr Ser Gly Ser Ser Phe Glu Asp Met Gly Glu
                20                  25                  30

Leu His Gln Arg Leu Arg Glu Glu Val Asp Ala Asp Ala Ala Ala
            35                  40                  45

Ala Glu Glu Asp Gly Glu Phe Leu Gly Met Lys Gly Phe Lys Gly
    50                  55                  60

Gln Leu Ser Arg Gln Val Ala Asp Gln Met Trp Gln Ala Gly Lys Arg
65                  70                  75                  80

Gln Ala Ser Arg Ala Phe Ser Leu Tyr Ala Asn Ile Asp Ile Leu Arg
                85                  90                  95

Pro Tyr Phe Asp Val Glu Pro Ala Gln Val Arg Ser Arg Leu Leu Glu
                100                 105                 110

Ser Met Ile Pro Ile Lys Met Val Asn Phe Pro Gln Lys Val Ala Gly
            115                 120                 125

Glu

<210> SEQ ID NO 25
<211> LENGTH: 330
<212> TYPE: PRT
<213> ORGANISM: Homo sapiens

<400> SEQUENCE: 25

Gly Phe Glu Glu Asn Ile Gln Gly Gly Ser Ala Val Ile Asp Met
1               5                   10                  15

Glu Asn Met Asp Asp Thr Ser Gly Ser Ser Phe Glu Asp Met Gly Glu
                20                  25                  30

Leu His Gln Arg Leu Arg Glu Glu Val Asp Ala Asp Ala Ala Asp
            35                  40                  45

Ala Ala Ala Glu Glu Glu Asp Gly Glu Phe Leu Gly Met Lys Gly
    50                  55                  60

Phe Lys Gly Gln Leu Ser Arg Gln Val Ala Asp Gln Met Trp Gln Ala
65                  70                  75                  80

Gly Lys Arg Gln Ala Ser Arg Ala Phe Ser Leu Tyr Ala Asn Ile Asp
                85                  90                  95

Ile Leu Arg Pro Tyr Phe Asp Val Glu Pro Ala Gln Val Arg Ser Arg
                100                 105                 110

Leu Leu Glu Ser Met Ile Pro Ile Lys Met Val Asn Phe Pro Gln Lys
            115                 120                 125

```
                                        -continued

Ile Ala Gly Glu Leu Tyr Gly Pro Leu Met Leu Val Leu Thr Leu Val
        130                 135                 140

Ala Ile Leu Leu His Gly Met Lys Thr Ser Asp Thr Ile Ile Arg Glu
145                     150                 155                 160

Gly Thr Leu Met Gly Thr Ala Ile Gly Thr Cys Phe Gly Tyr Trp Leu
                165                 170                 175

Gly Val Ser Ser Phe Ile Tyr Phe Leu Ala Tyr Leu Cys Asn Ala Gln
            180                 185                 190

Ile Thr Met Leu Gln Met Leu Ala Leu Leu Gly Tyr Gly Leu Phe Gly
        195                 200                 205

His Cys Ile Val Leu Phe Ile Thr Tyr Asn Ile His Leu His Ala Leu
    210                 215                 220

Phe Tyr Leu Phe Trp Leu Leu Val Gly Gly Leu Ser Thr Leu Arg Met
225                 230                 235                 240

Val Ala Val Leu Val Ser Arg Thr Val Gly Pro Thr Gln Arg Leu Leu
                245                 250                 255

Leu Cys Gly Thr Leu Ala Ala Leu His Met Leu Phe Leu Leu Tyr Leu
                260                 265                 270

His Phe Ala Tyr His Lys Val Val Glu Gly Ile Leu Asp Thr Leu Glu
            275                 280                 285

Gly Pro Asn Ile Pro Pro Ile Gln Arg Val Pro Arg Asp Ile Pro Ala
        290                 295                 300

Met Leu Pro Ala Ala Arg Leu Pro Thr Thr Val Leu Asn Ala Thr Ala
305                 310                 315                 320

Lys Ala Val Ala Val Thr Leu Gln Ser His
                325                 330
```